(12) United States Patent
Davila

(10) Patent No.: US 11,525,004 B2
(45) Date of Patent: *Dec. 13, 2022

(54) RECOMBINANT CD123-BINDING ANTIBODIES

(71) Applicant: H. Lee Moffitt Cancer Center and Research Institute, Inc., Tampa, FL (US)

(72) Inventor: Marco L. Davila, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 200 days.

This patent is subject to a terminal disclaimer.

(21) Appl. No.: 16/632,088

(22) PCT Filed: Jul. 18, 2018

(86) PCT No.: PCT/US2018/042709
§ 371 (c)(1),
(2) Date: Jan. 17, 2020

(87) PCT Pub. No.: WO2019/018538
PCT Pub. Date: Jan. 24, 2019

(65) Prior Publication Data
US 2020/0223930 A1 Jul. 16, 2020

Related U.S. Application Data

(60) Provisional application No. 62/534,957, filed on Jul. 20, 2017.

(51) Int. Cl.
*C07K 16/28* (2006.01)
(52) U.S. Cl.
CPC ...... *C07K 16/2866* (2013.01); *C07K 16/2809* (2013.01); *C07K 2317/565* (2013.01); *C07K 2317/622* (2013.01)

(58) Field of Classification Search
CPC ............ C07K 16/2866; C07K 16/2809; C07K 2317/565; C07K 2317/622
See application file for complete search history.

(56) References Cited

U.S. PATENT DOCUMENTS

| | | |
|---|---|---|
| 2005/0032175 A1 | 2/2005 | Stahl et al. |
| 2007/0123479 A1 | 5/2007 | Kufer et al. |
| 2010/0068199 A1 | 3/2010 | Liang et al. |
| 2016/0015749 A1* | 1/2016 | Gottschalk ....... A61K 39/39558 424/93.21 |

FOREIGN PATENT DOCUMENTS

| | | | |
|---|---|---|---|
| WO | 2009007427 A2 | 1/2009 | |
| WO | 2010016526 A1 | 2/2010 | |
| WO | 2012027723 A1 | 3/2012 | |
| WO | 2012031273 A2 | 3/2012 | |
| WO | 2016116626 A1 | 7/2016 | |
| WO | WO-2016116626 A1 * | 7/2016 | ......... C07K 16/2809 |
| WO | 2017035430 A2 | 3/2017 | |

OTHER PUBLICATIONS

International Search Report issued for application PCT/US2018/042709, dated Nov. 15, 2018.

* cited by examiner

*Primary Examiner* — Amy E Juedes
*Assistant Examiner* — Brian Hartnett
(74) *Attorney, Agent, or Firm* — Thomas | Horstemeyer, LLP

(57) ABSTRACT

Disclosed are compositions and methods for targeted treatment of CD123-expressing cancers. In particular, recombinant antibodies are disclosed that are able to engage T-cells to destroy CD123-expressing malignant cells.

11 Claims, 6 Drawing Sheets

Specification includes a Sequence Listing.

SEQUENCE LISTING

```
<160> NUMBER OF SEQ ID NOS: 60

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Gly Tyr Thr Phe Thr Asp Tyr Asn
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic Construct

<400> SEQUENCE: 2

Ile Asn Pro Asn Asn Gly Gly Thr
1               5

<210> SEQ ID NO 3
<211> LENGTH: 14
<212> TYPE: PRT
<213> ORGANISM: Artificial Sequence
<220> FEATURE:
<223> OTHER INFORMATION: Synthetic Construct

<400> SEQUENCE: 3

Ala Arg Lys Gly Tyr Gly Gly Asn Tyr Asp Tyr Phe Asp Tyr
1               5                   10

<210> SEQ ID NO 4
<211> LENGTH: 6
<212> TYPE: PRT
<213> ORGANISM: Artificial Sequence
```

```
<220> FEATURE:
<223> OTHER INFORMATION: Synthetic Construct

<400> SEQUENCE: 4

Gln Ser Ile Gly Thr Ser
1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 5

Tyr Ala Ser Xaa
1

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Gln Gln Ser Asn Ser Trp Pro Tyr Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Construct

<400> SEQUENCE: 7

Gly Phe Asn Ile Lys Asp Thr Tyr
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic Construct

<400> SEQUENCE: 8

Gly Phe Ser Leu Ser Thr Tyr Gly Met Gly
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Synthetic Construct

<400> SEQUENCE: 9

Ile Asp Pro Ala Asn Gly Asn Thr
1               5
```

```
<210> SEQ ID NO 10
<211> LENGTH: 7
<212> TYPE: PRT
<213> ORGANISM: Artificial Sequence
<220> FEATURE:
<223> OTHER INFORMATION: Synthetic Construct

<400> SEQUENCE: 10

Ile Tyr Trp Asp Asp Asp Lys
1               5

<210> SEQ ID NO 11
<211> LENGTH: 11
<212> TYPE: PRT
<213> ORGANISM: Artificial Sequence
<220> FEATURE:
<223> OTHER INFORMATION: Synthetic Construct

<400> SEQUENCE: 11

Ala Leu Tyr Tyr Tyr Gly Gly Ser Leu Asp Tyr
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetic Construct

<400> SEQUENCE: 12

Ala Gln Ser Leu Ile Tyr Asp Gly Tyr Tyr Gly Phe Ala Tyr
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic Construct

<400> SEQUENCE: 13

Gln Ser Leu Leu Tyr Ser Gly Asn Gln Lys Asn Tyr
1               5                   10

<210> SEQ ID NO 14
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 14

Trp Ala Ser Xaa
1

<210> SEQ ID NO 15
<211> LENGTH: 9
<212> TYPE: PRT
<213> ORGANISM: Artificial Sequence
<220> FEATURE:
<223> OTHER INFORMATION: Synthetic Construct
```

```
<400> SEQUENCE: 15

Gln Gln Tyr Tyr Ser Tyr Pro Arg Thr
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic Construct

<400> SEQUENCE: 16

Gly Tyr Thr Phe Thr Tyr Tyr Gly
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic Construct

<400> SEQUENCE: 17

Ile Asn Thr Tyr Ser Gly Val Pro
1               5

<210> SEQ ID NO 18
<211> LENGTH: 14
<212> TYPE: PRT
<213> ORGANISM: Artificial Sequence
<220> FEATURE:
<223> OTHER INFORMATION: Synthetic Construct

<400> SEQUENCE: 18

Ala Arg Trp Ile Tyr Tyr Ser Asp Leu Tyr Gly Met Asp Tyr
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic Construct

<400> SEQUENCE: 19

Gln Ser Ile Val His Ser Asn Gly Asp Thr Tyr
1               5                   10

<210> SEQ ID NO 20
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 20

Lys Val Ser Xaa
1

<210> SEQ ID NO 21
<211> LENGTH: 9
<212> TYPE: PRT
<213> ORGANISM: Artificial Sequence
```

-continued

<220> FEATURE:
<223> OTHER INFORMATION: Synthetic Construct

<400> SEQUENCE: 21

Phe Gln Gly Ser His Val Pro Trp Thr
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic Construct

<400> SEQUENCE: 22

Gly Tyr Thr Phe Ser Ser Tyr Trp
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic Construct

<400> SEQUENCE: 23

Gly Tyr Thr Leu Thr Thr Tyr Leu
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic Construct

<400> SEQUENCE: 24

Ile Asn Pro Ser Ser Gly Tyr Thr
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic Construct

<400> SEQUENCE: 25

Ile Asn Pro Asn Ser Gly Ser Ser
1               5

<210> SEQ ID NO 26
<211> LENGTH: 13
<212> TYPE: PRT
<213> ORGANISM: Artificial Sequence
<220> FEATURE:
<223> OTHER INFORMATION: Synthetic Construct

<400> SEQUENCE: 26

Ala Arg Asp Gly Asn Tyr Asp His Trp Tyr Phe Asp Val
1               5                   10

<210> SEQ ID NO 27
<211> LENGTH: 12
<212> TYPE: PRT
<213> ORGANISM: Artificial Sequence

```
<220> FEATURE:
<223> OTHER INFORMATION: Synthetic Construct

<400> SEQUENCE: 27

Ala Ile Arg His Tyr Gly Gly Ser Leu Phe Asp Tyr
1               5                   10

<210> SEQ ID NO 28
<211> LENGTH: 6
<212> TYPE: PRT
<213> ORGANISM: Artificial Sequence
<220> FEATURE:
<223> OTHER INFORMATION: Synthetic Construct

<400> SEQUENCE: 28

Gln Asp Ile Asn Ser Tyr
1               5

<210> SEQ ID NO 29
<211> LENGTH: 12
<212> TYPE: PRT
<213> ORGANISM: Artificial Sequence
<220> FEATURE:
<223> OTHER INFORMATION: Synthetic Construct

<400> SEQUENCE: 29

Gln Ser Leu Leu Asn Ser Arg Thr Arg Lys Asn Tyr
1               5                   10

<210> SEQ ID NO 30
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 30

Arg Ala Asn Xaa
1

<210> SEQ ID NO 31
<211> LENGTH: 8
<212> TYPE: PRT
<213> ORGANISM: Artificial Sequence
<220> FEATURE:
<223> OTHER INFORMATION: Synthetic Construct

<400> SEQUENCE: 31

Leu Gln Tyr Asp Glu Leu Leu Thr
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic Construct

<400> SEQUENCE: 32

Glu Gln Ser Tyr Asn Leu Phe Thr
1               5
```

```
<210> SEQ ID NO 33
<211> LENGTH: 121
<212> TYPE: PRT
<213> ORGANISM: Artificial Sequence
<220> FEATURE:
<223> OTHER INFORMATION: Synthetic Construct

<400> SEQUENCE: 33

Glu Val Gln Leu Gln Gln Ser Gly Pro Glu Leu Val Lys Pro Gly Ser
1               5                   10                  15

Ser Val Lys Ile Ser Cys Lys Ala Ser Gly Tyr Thr Phe Thr Asp Tyr
                20                  25                  30

Asn Met Asp Trp Val Lys Gln Ser His Gly Lys Ser Leu Glu Trp Ile
            35                  40                  45

Gly Thr Ile Asn Pro Asn Asn Gly Gly Thr Ser Tyr Asn Gln Lys Phe
        50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Lys Gly Tyr Gly Gly Asn Tyr Asp Tyr Phe Asp Tyr Trp Gly
                100                 105                 110

Gln Gly Thr Thr Leu Thr Val Ser Ser
        115                 120

<210> SEQ ID NO 34
<211> LENGTH: 118
<212> TYPE: PRT
<213> ORGANISM: Artificial Sequence
<220> FEATURE:
<223> OTHER INFORMATION: Synthetic Construct

<400> SEQUENCE: 34

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
                20                  25                  30

Tyr Met His Trp Val Lys Gln Arg Pro Glu Gln Gly Leu Glu Trp Ile
            35                  40                  45

Gly Arg Ile Asp Pro Ala Asn Gly Asn Thr Ile Tyr Ala Ser Lys Phe
        50                  55                  60

Gln Gly Lys Ala Thr Ile Thr Ala Asp Thr Ser Ser Asn Thr Ala Tyr
65                  70                  75                  80

Met Gln Leu Ser Ser Leu Thr Ser Gly Asp Thr Ala Val Tyr Tyr Cys
                85                  90                  95

Ala Leu Tyr Tyr Tyr Gly Gly Ser Leu Asp Tyr Trp Gly Gln Gly Thr
                100                 105                 110

Thr Leu Thr Val Ser Ser
        115

<210> SEQ ID NO 35
<211> LENGTH: 122
<212> TYPE: PRT
<213> ORGANISM: Artificial Sequence
<220> FEATURE:
<223> OTHER INFORMATION: Synthetic Construct
```

```
<400> SEQUENCE: 35

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Asn Asn Gln Val
65                  70                  75                  80

Phe Leu Lys Ile Thr Ser Val Asp Thr Ala Asp Ala Thr Tyr Tyr
                85                  90                  95

Cys Ala Gln Ser Leu Ile Tyr Asp Gly Tyr Tyr Gly Phe Ala Tyr Trp
                100                 105                 110

Gly Gln Gly Thr Leu Val Thr Val Ser Ala
            115                 120

<210> SEQ ID NO 36
<211> LENGTH: 121
<212> TYPE: PRT
<213> ORGANISM: Artificial Sequence
<220> FEATURE:
<223> OTHER INFORMATION: Synthetic Construct

<400> SEQUENCE: 36

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Tyr Tyr
            20                  25                  30

Gly Met Asn Trp Val Lys Gln Ala Pro Gly Lys Gly Leu Glu Trp Met
        35                  40                  45

Gly Trp Ile Asn Thr Tyr Ser Gly Val Pro Thr Tyr Ala Asp Asp Phe
    50                  55                  60

Lys Gly Arg Phe Ala Phe Ser Leu Glu Thr Ser Val Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Trp Ile Tyr Tyr Ser Asp Leu Tyr Gly Met Asp Tyr Trp Gly
                100                 105                 110

Gln Gly Thr Ser Val Thr Val Ser Ser
            115                 120

<210> SEQ ID NO 37
<211> LENGTH: 120
<212> TYPE: PRT
<213> ORGANISM: Artificial Sequence
<220> FEATURE:
<223> OTHER INFORMATION: Synthetic Construct

<400> SEQUENCE: 37

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Ser Ser Tyr
            20                  25                  30

Trp Met His Trp Leu Lys Gln Arg Pro Gly Gln Gly Leu Glu Trp Ile
        35                  40                  45
```

Gly Tyr Ile Asn Pro Ser Ser Gly Tyr Thr Asn Tyr Asn Gln Lys Phe
            50                  55                  60

Lys Asp Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Tyr Cys
                85                  90                  95

Ala Arg Asp Gly Asn Tyr Asp His Trp Tyr Phe Asp Val Trp Gly Thr
            100                 105                 110

Gly Thr Thr Val Thr Val Ser Ser
            115                 120

<210> SEQ ID NO 38
<211> LENGTH: 119
<212> TYPE: PRT
<213> ORGANISM: Artificial Sequence
<220> FEATURE:
<223> OTHER INFORMATION: Synthetic Construct

<400> SEQUENCE: 38

Gln Val Gln Leu Gln Gln Pro Gly Ala Glu Leu Val Arg Pro Gly Ala
 1               5                   10                  15

Ser Val Lys Met Ser Cys Lys Ala Ser Gly Tyr Thr Leu Thr Thr Tyr
                20                  25                  30

Leu Met Asp Trp Val Lys Gln Arg Leu Gly Gln Gly Phe Glu Trp Ile
            35                  40                  45

Gly Asn Ile Asn Pro Asn Ser Gly Ser Ser Asn Tyr Asn Glu Lys Phe
        50                  55                  60

Lys Gly Lys Ala Lys Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                85                  90                  95

Ala Ile Arg His Tyr Gly Gly Ser Leu Phe Asp Tyr Trp Gly Gln Gly
            100                 105                 110

Thr Thr Leu Thr Val Ser Ser
            115

<210> SEQ ID NO 39
<211> LENGTH: 107
<212> TYPE: PRT
<213> ORGANISM: Artificial Sequence
<220> FEATURE:
<223> OTHER INFORMATION: Synthetic Construct

<400> SEQUENCE: 39

Asp Ile Leu Leu Thr Gln Ser Pro Ala Ile Leu Ser Val Ser Pro Gly
 1               5                   10                  15

Glu Arg Val Ser Phe Ser Cys Arg Ala Ser Gln Ser Ile Gly Thr Ser
                20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Ser Asn Ser Trp Pro Tyr
                85                  90                  95

Thr Phe Gly Gly Gly Thr Lys Leu Glu Ile Lys
            100                 105

```
<210> SEQ ID NO 40
<211> LENGTH: 113
<212> TYPE: PRT
<213> ORGANISM: Artificial Sequence
<220> FEATURE:
<223> OTHER INFORMATION: Synthetic Construct

<400> SEQUENCE: 40

Asp Ile Val Met Ser Gln Ser Pro Ser Ser Leu Ala Val Ser Val Gly
1               5                   10                  15

Glu Arg Val Thr Met Ser Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Arg Thr Phe Gly Gly Gly Thr Lys Leu Glu Ile
            100                 105                 110

Lys

<210> SEQ ID NO 41
<211> LENGTH: 112
<212> TYPE: PRT
<213> ORGANISM: Artificial Sequence
<220> FEATURE:
<223> OTHER INFORMATION: Synthetic Construct

<400> SEQUENCE: 41

Asp Val Leu Met Thr Gln Ser Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asp Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr His Cys Phe Gln Gly
                85                  90                  95

Ser His Val Pro Trp Thr Phe Gly Gly Gly Thr Lys Leu Glu Ile Lys
            100                 105                 110

<210> SEQ ID NO 42
<211> LENGTH: 106
<212> TYPE: PRT
<213> ORGANISM: Artificial Sequence
<220> FEATURE:
<223> OTHER INFORMATION: Synthetic Construct

<400> SEQUENCE: 42

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30
```

Leu Ser Trp Phe Gln Gln Lys Pro Gly Lys Ser Pro Lys Thr Leu Ile
          35                  40                  45

Tyr Arg Ala Asn Arg Leu Val Asp Gly Val Pro Ser Arg Phe Ser Gly
 50                  55                  60

Ser Gly Ser Gly Gln Asp Tyr Ser Leu Thr Ile Ser Ser Leu Glu Tyr
 65                  70                  75                  80

Glu Asp Met Gly Ile Tyr Tyr Cys Leu Gln Tyr Asp Glu Leu Leu Thr
             85                  90                  95

Phe Gly Ala Gly Thr Lys Leu Glu Leu Lys
            100                 105

<210> SEQ ID NO 43
<211> LENGTH: 112
<212> TYPE: PRT
<213> ORGANISM: Artificial Sequence
<220> FEATURE:
<223> OTHER INFORMATION: Synthetic Construct

<400> SEQUENCE: 43

Asp Ile Val Met Ser Gln Ser Pro Ser Ser Leu Ala Val Ser Ala Gly
 1               5                  10                  15

Glu Arg Val Thr Met Ser Cys Arg Ser Ser Gln Ser Leu Leu Asn Ser
             20                  25                  30

Arg Thr Arg Lys Asn Tyr Leu Ala Trp Tyr Gln Gln Lys Pro Gly Gln
         35                  40                  45

Ser Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Val Gln Ala Glu Asp Leu Ala Val Tyr Tyr Cys Glu Gln
             85                  90                  95

Ser Tyr Asn Leu Phe Thr Phe Gly Ser Gly Thr Lys Leu Glu Ile Lys
            100                 105                 110

<210> SEQ ID NO 44
<211> LENGTH: 243
<212> TYPE: PRT
<213> ORGANISM: Artificial Sequence
<220> FEATURE:
<223> OTHER INFORMATION: Synthetic Construct

<400> SEQUENCE: 44

Glu Val Gln Leu Gln Gln Ser Gly Pro Glu Leu Val Lys Pro Gly Ser
 1               5                  10                  15

Ser Val Lys Ile Ser Cys Lys Ala Ser Gly Tyr Thr Phe Thr Asp Tyr
             20                  25                  30

Asn Met Asp Trp Val Lys Gln Ser His Gly Lys Ser Leu Glu Trp Ile
         35                  40                  45

Gly Thr Ile Asn Pro Asn Asn Gly Gly Thr Ser Tyr Asn Gln Lys Phe
 50                  55                  60

Lys Gly Lys Ala Thr Leu Thr Val Asp Lys Ser Ser Ser Thr Ala Tyr
 65                  70                  75                  80

Met Glu Leu Arg Ser Leu Thr Ser Glu Asp Ser Ala Val Tyr Tyr Cys
             85                  90                  95

Ala Arg Lys Gly Tyr Gly Gly Asn Tyr Asp Tyr Phe Asp Tyr Trp Gly
            100                 105                 110

Gln Gly Thr Thr Leu Thr Val Ser Ser Gly Gly Gly Gly Ser Gly Gly
            115                 120                 125

```
Gly Gly Ser Gly Gly Gly Ser Asp Ile Leu Thr Gln Ser Pro
    130             135             140

Ala Ile Leu Ser Val Ser Pro Gly Glu Arg Val Ser Phe Ser Cys Arg
145             150             155             160

Ala Ser Gln Ser Ile Gly Thr Ser Ile His Trp Tyr Gln Gln Arg Thr
                165             170             175

Asn Gly Ser Pro Arg Leu Leu Ile Lys Tyr Ala Ser Glu Ser Ile Ser
            180             185             190

Gly Ile Pro Ser Arg Phe Ser Gly Ser Gly Ser Gly Thr Asp Phe Thr
        195             200             205

Leu Ser Ile Asn Ser Val Glu Ser Glu Asp Ile Ala Asp Tyr Tyr Cys
210             215             220

Gln Gln Ser Asn Ser Trp Pro Tyr Thr Phe Gly Gly Gly Thr Lys Leu
225             230             235             240

Glu Ile Lys

<210> SEQ ID NO 45
<211> LENGTH: 246
<212> TYPE: PRT
<213> ORGANISM: Artificial Sequence
<220> FEATURE:
<223> OTHER INFORMATION: Synthetic Construct

<400> SEQUENCE: 45

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Ile Tyr Ala Ser Lys Phe
    50                  55                  60

Gln Gly Lys Ala Thr Ile Thr Ala Asp Thr Ser Ser Asn Thr Ala Tyr
65                  70                  75                  80

Met Gln Leu Ser Ser Leu Thr Ser Gly Asp Thr Ala Val Tyr Tyr Cys
                85                  90                  95

Ala Leu Tyr Tyr Tyr Gly Gly Ser Leu Asp Tyr Trp Gly Gln Gly Thr
            100                 105                 110

Thr Leu Thr Val Ser Ser Gly Gly Gly Gly Ser Gly Gly Gly Gly Ser
        115                 120                 125

Gly Gly Gly Gly Ser Asp Ile Val Met Ser Gln Ser Pro Ser Ser Leu
    130                 135                 140

Ala Val Ser Val Gly Glu Arg Val Thr Met Ser Cys Lys Ser Ser Gln
145                 150                 155                 160

Ser Leu Leu Tyr Ser Gly Asn Gln Lys Asn Tyr Leu Ala Trp Tyr Gln
                165                 170                 175

Gln Lys Pro Gly Gln Ser Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Lys Ala Glu Asp Leu Ala Val
    210                 215                 220
```

Tyr Tyr Cys Gln Gln Tyr Ser Tyr Pro Arg Thr Phe Gly Gly Gly
225                 230                 235                 240

Thr Lys Leu Glu Ile Lys
            245

<210> SEQ ID NO 46
<211> LENGTH: 250
<212> TYPE: PRT
<213> ORGANISM: Artificial Sequence
<220> FEATURE:
<223> OTHER INFORMATION: Synthetic Construct

<400> SEQUENCE: 46

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Asn Asn Gln Val
65                  70                  75                  80

Phe Leu Lys Ile Thr Ser Val Asp Thr Ala Asp Thr Ala Thr Tyr Tyr
                85                  90                  95

Cys Ala Gln Ser Leu Ile Tyr Asp Gly Tyr Tyr Gly Phe Ala Tyr Trp
            100                 105                 110

Gly Gln Gly Thr Leu Val Thr Val Ser Ala Gly Gly Gly Gly Ser Gly
        115                 120                 125

Gly Gly Gly Ser Gly Gly Gly Gly Ser Asp Ile Val Met Ser Gln Ser
    130                 135                 140

Pro Ser Ser Leu Ala Val Ser Val Gly Glu Arg Val Thr Met Ser Cys
145                 150                 155                 160

Lys Ser Ser Gln Ser Leu Leu Tyr Ser Gly Asn Gln Lys Asn Tyr Leu
                165                 170                 175

Ala Trp Tyr Gln Gln Lys Pro Gly Gln Ser Pro Lys Leu Leu Ile Tyr
            180                 185                 190

Trp Ala Ser Thr Arg Glu Ser Gly Val Pro Asp Arg Phe Thr Gly Ser
        195                 200                 205

Gly Ser Gly Thr Asp Phe Thr Leu Thr Ile Ser Ser Val Lys Ala Glu
    210                 215                 220

Asp Leu Ala Val Tyr Tyr Cys Gln Gln Tyr Tyr Ser Tyr Pro Arg Thr
225                 230                 235                 240

Phe Gly Gly Gly Thr Lys Leu Glu Ile Lys
                245                 250

<210> SEQ ID NO 47
<211> LENGTH: 248
<212> TYPE: PRT
<213> ORGANISM: Artificial Sequence
<220> FEATURE:
<223> OTHER INFORMATION: Synthetic Construct

<400> SEQUENCE: 47

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Tyr Tyr
            20                  25                  30

Gly Met Asn Trp Val Lys Gln Ala Pro Gly Lys Gly Leu Glu Trp Met
            35                  40                  45

Gly Trp Ile Asn Thr Tyr Ser Gly Val Pro Thr Tyr Ala Asp Asp Phe
 50                  55                  60

Lys Gly Arg Phe Ala Phe Ser Leu Glu Thr Ser Val Ser Thr Ala Tyr
 65                  70                  75                  80

Leu Gln Ile Asn Asn Leu Lys Asn Glu Asp Thr Ala Thr Tyr Phe Cys
                 85                  90                  95

Ala Arg Trp Ile Tyr Tyr Ser Asp Leu Tyr Gly Met Asp Tyr Trp Gly
            100                 105                 110

Gln Gly Thr Ser Val Thr Val Ser Ser Gly Gly Gly Ser Gly Gly
            115                 120                 125

Gly Gly Ser Gly Gly Gly Ser Asp Val Leu Met Thr Gln Ser Pro
130                 135                 140

Leu Ser Leu Pro Val Ser Leu Gly Asp Gln Ala Ser Ile Ser Cys Arg
145                 150                 155                 160

Ser Ser Gln Ser Ile Val His Ser Asn Gly Asp Thr Tyr Leu Glu Trp
                165                 170                 175

Tyr Leu Gln Lys Pro Gly Gln Ser Pro Lys Leu Leu Ile Tyr Lys Val
            180                 185                 190

Ser Asn Arg Phe Ser Gly Val Pro Asp Arg Phe Ser Gly Ser Gly Ser
            195                 200                 205

Gly Thr Asp Phe Thr Leu Lys Ile Ser Arg Val Glu Ala Glu Asp Leu
            210                 215                 220

Gly Val Tyr His Cys Phe Gln Gly Ser His Val Pro Trp Thr Phe Gly
225                 230                 235                 240

Gly Gly Thr Lys Leu Glu Ile Lys
                245

<210> SEQ ID NO 48
<211> LENGTH: 241
<212> TYPE: PRT
<213> ORGANISM: Artificial Sequence
<220> FEATURE:
<223> OTHER INFORMATION: Synthetic Construct

<400> SEQUENCE: 48

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Ser Ser Tyr
            20                  25                  30

Trp Met His Trp Leu Lys Gln Arg Pro Gly Gln Gly Leu Glu Trp Ile
            35                  40                  45

Gly Tyr Ile Asn Pro Ser Ser Gly Tyr Thr Asn Tyr Asn Gln Lys Phe
 50                  55                  60

Lys Asp Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Asp Gly Asn Tyr Asp His Trp Tyr Phe Asp Val Trp Gly Thr
            100                 105                 110

Gly Thr Thr Val Thr Val Ser Ser Gly Gly Gly Gly Ser Gly Gly Gly
            115                 120                 125

Gly Ser Gly Gly Gly Gly Ser Asp Ile Lys Met Thr Gln Ser Pro Ser
            130                 135                 140

```
Ser Met Tyr Ala Ser Leu Gly Glu Arg Val Thr Ile Thr Cys Lys Ala
145                 150                 155                 160

Ser Gln Asp Ile Asn Ser Tyr Leu Ser Trp Phe Gln Gln Lys Pro Gly
                165                 170                 175

Lys Ser Pro Lys Thr Leu Ile Tyr Arg Ala Asn Arg Leu Val Asp Gly
            180                 185                 190

Val Pro Ser Arg Phe Ser Gly Ser Gly Ser Gly Gln Asp Tyr Ser Leu
        195                 200                 205

Thr Ile Ser Ser Leu Glu Tyr Glu Asp Met Gly Ile Tyr Tyr Cys Leu
    210                 215                 220

Gln Tyr Asp Glu Leu Leu Thr Phe Gly Ala Gly Thr Lys Leu Glu Leu
225                 230                 235                 240

Lys
```

```
<210> SEQ ID NO 49
<211> LENGTH: 247
<212> TYPE: PRT
<213> ORGANISM: Artificial Sequence
<220> FEATURE:
<223> OTHER INFORMATION: Synthetic Construct

<400> SEQUENCE: 49

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Ser Ser Tyr
                20                  25                  30

Trp Met His Trp Leu Lys Gln Arg Pro Gly Gln Gly Leu Glu Trp Ile
            35                  40                  45

Gly Tyr Ile Asn Pro Ser Ser Gly Tyr Thr Asn Tyr Asn Gln Lys Phe
        50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Gly Asn Tyr Asp His Trp Tyr Phe Asp Val Trp Gly Thr
            100                 105                 110

Gly Thr Thr Val Thr Val Ser Ser Gly Gly Gly Gly Ser Gly Gly Gly
        115                 120                 125

Gly Ser Gly Gly Gly Gly Ser Asp Ile Val Met Ser Gln Ser Pro Ser
    130                 135                 140

Ser Leu Ala Val Ser Ala Gly Glu Arg Val Thr Met Ser Cys Arg Ser
145                 150                 155                 160

Ser Gln Ser Leu Leu Asn Ser Arg Thr Arg Lys Asn Tyr Leu Ala Trp
                165                 170                 175

Tyr Gln Gln Lys Pro Gly Gln Ser Pro Lys Leu Leu Ile Tyr Trp Ala
            180                 185                 190

Ser Thr Arg Glu Ser Gly Val Pro Asp Arg Phe Ser Gly Ser Gly Ser
        195                 200                 205

Gly Thr Asp Phe Thr Leu Thr Ile Ser Ser Val Gln Ala Glu Asp Leu
    210                 215                 220

Ala Val Tyr Tyr Cys Glu Gln Ser Tyr Asn Leu Phe Thr Phe Gly Ser
225                 230                 235                 240

Gly Thr Lys Leu Glu Ile Lys
                245
```

<210> SEQ ID NO 50
<211> LENGTH: 240
<212> TYPE: PRT
<213> ORGANISM: Artificial Sequence
<220> FEATURE:
<223> OTHER INFORMATION: Synthetic Construct

<400> SEQUENCE: 50

```
Gln Val Gln Leu Gln Gln Pro Gly Ala Glu Leu Val Arg Pro Gly Ala
1               5                   10                  15

Ser Val Lys Met Ser Cys Lys Ala Ser Gly Tyr Thr Leu Thr Thr Tyr
            20                  25                  30

Leu Met Asp Trp Val Lys Gln Arg Leu Gly Gln Gly Phe Glu Trp Ile
        35                  40                  45

Gly Asn Ile Asn Pro Asn Ser Gly Ser Ser Asn Tyr Asn Glu Lys Phe
    50                  55                  60

Lys Gly Lys Ala Lys Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ile Arg His Tyr Gly Gly Ser Leu Phe Asp Tyr Trp Gly Gln Gly
            100                 105                 110

Thr Thr Leu Thr Val Ser Ser Gly Gly Gly Ser Gly Gly Gly Gly
        115                 120                 125

Ser Gly Gly Gly Gly Ser Asp Ile Lys Met Thr Gln Ser Pro Ser Ser
    130                 135                 140

Met Tyr Ala Ser Leu Gly Glu Arg Val Thr Ile Thr Cys Lys Ala Ser
145                 150                 155                 160

Gln Asp Ile Asn Ser Tyr Leu Ser Trp Phe Gln Gln Lys Pro Gly Lys
                165                 170                 175

Ser Pro Lys Thr Leu Ile Tyr Arg Ala Asn Arg Leu Val Asp Gly Val
            180                 185                 190

Pro Ser Arg Phe Ser Gly Ser Gly Ser Gly Gln Asp Tyr Ser Leu Thr
        195                 200                 205

Ile Ser Ser Leu Glu Tyr Glu Asp Met Gly Ile Tyr Tyr Cys Leu Gln
    210                 215                 220

Tyr Asp Glu Leu Leu Thr Phe Gly Ala Gly Thr Lys Leu Glu Leu Lys
225                 230                 235                 240
```

<210> SEQ ID NO 51
<211> LENGTH: 246
<212> TYPE: PRT
<213> ORGANISM: Artificial Sequence
<220> FEATURE:
<223> OTHER INFORMATION: Synthetic Construct

<400> SEQUENCE: 51

```
Gln Val Gln Leu Gln Gln Pro Gly Ala Glu Leu Val Arg Pro Gly Ala
1               5                   10                  15

Ser Val Lys Met Ser Cys Lys Ala Ser Gly Tyr Thr Leu Thr Thr Tyr
            20                  25                  30

Leu Met Asp Trp Val Lys Gln Arg Leu Gly Gln Gly Phe Glu Trp Ile
        35                  40                  45

Gly Asn Ile Asn Pro Asn Ser Gly Ser Ser Asn Tyr Asn Glu Lys Phe
    50                  55                  60

Lys Gly Lys Ala Lys Leu Thr Val Asp Lys Ser Ser Ser Thr Ala Tyr
65                  70                  75                  80
```

```
Met Gln Leu Ser Ser Leu Thr Ser Glu Asp Ser Ala Val Tyr Tyr Cys
                85                  90                  95

Ala Ile Arg His Tyr Gly Gly Ser Leu Phe Asp Tyr Trp Gly Gln Gly
            100                 105                 110

Thr Thr Leu Thr Val Ser Ser Gly Gly Gly Ser Gly Gly Gly Gly
        115                 120                 125

Ser Gly Gly Gly Ser Asp Ile Val Met Gln Ser Pro Ser Ser
    130                 135                 140

Leu Ala Val Ser Ala Gly Glu Arg Val Thr Met Ser Cys Arg Ser Ser
145                 150                 155                 160

Gln Ser Leu Leu Asn Ser Arg Thr Arg Lys Asn Tyr Leu Ala Trp Tyr
                165                 170                 175

Gln Gln Lys Pro Gly Gln Ser Pro Lys Leu Leu Ile Tyr Trp Ala Ser
            180                 185                 190

Thr Arg Glu Ser Gly Val Pro Asp Arg Phe Ser Gly Ser Gly Ser Gly
        195                 200                 205

Thr Asp Phe Thr Leu Thr Ile Ser Ser Val Gln Ala Glu Asp Leu Ala
    210                 215                 220

Val Tyr Tyr Cys Glu Gln Ser Tyr Asn Leu Phe Thr Phe Gly Ser Gly
225                 230                 235                 240

Thr Lys Leu Glu Ile Lys
                245

<210> SEQ ID NO 52
<211> LENGTH: 795
<212> TYPE: DNA
<213> ORGANISM: Artificial Sequence
<220> FEATURE:
<223> OTHER INFORMATION: Synthetic Construct

<400> SEQUENCE: 52
atggccctcc cggtaacggc tctgctgctt ccactcgcac tgctcttgca tgctgccaga      60
ccagaggtcc agctgcaaca gtctggacct gagctggtga agcctgggtc ttcagtgaag     120
atatcctgca agcttctgg atacacattc actgactaca acatggactg ggtgaagcag     180
agtcatggaa agagccttga gtggattgga actattaatc ctaacaatgg tggtactagc     240
tacaaccaga gttcaaggg caaggccaca ttgactgtag acaagtcctc cagcacagcc     300
tacatggagc tccgcagcct gacatctgaa gactctgcag tctattactg tgcaagaaag     360
ggctatggtg gtaactacga ctactttgac tactggggcc aaggcaccac tctcacagtc     420
tcctcaggtg gaggtggatc aggtggaggt ggatctggtg gaggtggatc tgacatcttg     480
ctgactcagt ctccagccat cctgtctgtg agtccaggag aaagagtcag tttctcctgc     540
agggccagtc agagcattgg cacaagcata cactggtatc agcaaagaac aaatggttct     600
ccaaggcttc tcataaagta tgcttctgag tctatctctg ggttcccttc caggtttagt     660
ggcagtggat cagggacaga tttttactctt agcatcaaca gtgtgagtc tgaagatatt     720 gcagattatt actgtcaaca aagtaatagc tggccgtaca cgttcggagg ggggaccaag     780
ctggaaataa aacgg                                                      795

<210> SEQ ID NO 53
<211> LENGTH: 804
<212> TYPE: DNA
<213> ORGANISM: Artificial Sequence
<220> FEATURE:
<223> OTHER INFORMATION: Synthetic Construct
```

<400> SEQUENCE: 53

```
atggccctcc cggtaacggc tctgctgctt ccactcgcac tgctcttgca tgctgccaga    60
ccagaggttc agctgcagca gtctggggca gagcttgtga agccagggc ctcagtcaag    120
ttgtcctgca cagcttctgg cttcaacatt aaagacacct atatgcactg ggtgaagcag    180
aggcctgaac agggcctgga gtggattgga aggattgatc ctgcgaatgg taatactata    240
tatgcctcaa agttccaggg caaggccact ataacagcag acacatcatc aacacagcc    300
tacatgcagc tcagcagcct gacatctggg gacactgccg tctattactg tgctctttat    360
tactatggtg gtagccttga ctactggggc caaggcacca ctctcacagt ctcctcaggt    420
ggaggtggat caggtggagg tggatctggt ggaggtggat ctgacattgt gatgtcacag    480
tctccatcct ccctagctgt gtcagttgga gagagggtta ctatgagctg caagtccagt    540
cagagccttt atatagtgg caatcaaaag aactacttgg cctggtacca gcagaaacca    600
gggcagtctc ctaaactgct gatttactgg gcatccacta gggaatctgg ggtccctgat    660
cgcttcacag gcagtggatc tgggacagat ttcactctca ccatcagcag tgtgaaggct    720
gaagacctgg cagtttatta ctgtcagcaa tattatagct atcctcggac gttcggtgga    780
ggcaccaagc tggaaatcaa acgg                                           804
```

<210> SEQ ID NO 54
<211> LENGTH: 816
<212> TYPE: DNA
<213> ORGANISM: Artificial Sequence
<220> FEATURE:
<223> OTHER INFORMATION: Synthetic Construct

<400> SEQUENCE: 54

```
atggccctcc cggtaacggc tctgctgctt ccactcgcac tgctcttgca tgctgccaga    60
ccacaggtta ctctgaaaga gtctggccct gggatattgc agccctccca gaccctcagt    120
ctgacttgtt ctttctctgg gttttcactg agcacttatg gtatgggtgt gagctggatt    180
cgtcagcctt caggaaaggg tctggagtgg ctggcacaca tttactggga tgatgacaag    240
cgctataacc catccctgaa gagccggctc acaatctcca aggataccctc caacaaccag    300
gtattcctca agatcaccag tgtggacact gcagatactg ccacatacta ctgtgctcaa    360
agcctgatct atgatggtta ctacgggttt gcctactggg gccaaggac tctggtcact    420
gtctctgcag gtggaggtgg atcaggtgga ggtggatctg gtggaggtgg atctgacatt    480
gtgatgtcac agtctccatc ctccctagct gtgtcagttg gagagagggt tactatgagc    540
tgcaagtcca gtcagagcct tttatatagt ggcaatcaaa agaactactt ggcctggtac    600
cagcagaaac agggcagtc tcctaaactg ctgatttact gggcatccac tagggaatct    660
ggggtccctg atcgcttcac aggcagtgga tctgggacag atttcactct caccatcagc    720
agtgtgaagg ctgaagacct ggcagtttat tactgtcagc aatattatag ctatcctcgg    780
acgttcggtg gaggcaccaa gctggaaatc aaacgg                              816
```

<210> SEQ ID NO 55
<211> LENGTH: 810
<212> TYPE: DNA
<213> ORGANISM: Artificial Sequence
<220> FEATURE:
<223> OTHER INFORMATION: Synthetic Construct

<400> SEQUENCE: 55

```
atggccctcc cggtaacggc tctgctgctt ccactcgcac tgctcttgca tgctgccaga      60
ccacagatcc agttggtgca atctggacct gagctgaaga agcctggaga cagtcaag      120
atctcctgca aggcttctgg gtataccttc acatactatg aatgaactg ggtgaagcag     180
gctccaggaa agggtttaga gtggatgggc tggataaaca cctactctgg agtgccaaca    240
tatgctgatg acttcaaggg acggtttgcc ttctctttgg aaacctctgt cagcactgcc    300
tatttgcaga tcaacaacct caaaaatgag acacggcta catattttg tgcaagatgg      360
atctactata gtgacctcta tggtatggac tactggggtc aaggaacctc agtcaccgtc    420
tcctcaggtg aggtggatc aggtggaggt ggatctggtg aggtggatc tgatgttttg     480
atgacccaaa gtccactctc cctgcctgtc agtcttggag atcaagcctc catctcttgt   540
agatctagtc agagtattgt acatagtaat ggagacacgt atttagaatg gtatttgcag   600
aaaccaggcc agtctccaaa gctcctgatc tacaaagttt ctaaccgatt ttctggggtc   660
ccagacaggt tcagtggcag tggatcaggg acagattca cactcaagat cagcagagtg    720
gaggctgagg atctgggagt ttatcactgc tttcaaggtt cacatgttcc gtggacgttc   780
ggtggaggca ccaagctgga atcaaacgg                                      810
```

<210> SEQ ID NO 56
<211> LENGTH: 789
<212> TYPE: DNA
<213> ORGANISM: Artificial Sequence
<220> FEATURE:
<223> OTHER INFORMATION: Synthetic Construct

<400> SEQUENCE: 56

```
atggccctcc cggtaacggc tctgctgctt ccactcgcac tgctcttgca tgctgccaga      60
ccacaggtcc agctgcagca gtctggggct gaactggcaa acctggggc ctcagtgaag     120
atgtcctgca aggcttctgg ctacaccttt tctagctact ggatgcactg gctaaaacag    180
aggcctggac agggtctgga gtggattgga tacattaatc ctagcagtgg ttatactaac   240
tacaatcaga gttcaagga caaggccaca ttgactgcag acaaatcctc cagcacagcc    300
tacatgcaac tgagcagcct gacatctgag gactctgcag tctattactg tgcaagagat   360
ggtaactatg accactggta cttcgatgtc tggggcacag ggaccacggt caccgtctcc   420
tcaggtggag gtggatcagg tggaggtgga tctggtggag gtggatctga catcaagatg   480
acccagtctc catcttccat gtatgcatct ctaggagaga gagtcactat cacttgcaag   540
gcgagtcagg acattaatag ctatttaagc tggttccagc agaaaccagg gaaatctcct   600
aagaccctga tctatcgtgc aaacagattg gtagatgggg tcccatcaag gttcagtggc   660
agtggatctg ggcaagatta ttctctcacc atcagcagcc tggagtatga agatatggga   720
atttattatt gtctacagta tgatgagttg ctcacgttcg gtgctgggac caagctggag   780
ctgaaacgg                                                            789
```

<210> SEQ ID NO 57
<211> LENGTH: 807
<212> TYPE: DNA
<213> ORGANISM: Artificial Sequence
<220> FEATURE:
<223> OTHER INFORMATION: Synthetic Construct

<400> SEQUENCE: 57

```
atggccctcc cggtaacggc tctgctgctt ccactcgcac tgctcttgca tgctgccaga      60
ccacaggtcc agctgcagca gtctggggct gaactggcaa acctggggc ctcagtgaag      120
atgtcctgca aggcttctgg ctacaccttt tctagctact ggatgcactg gctaaaacag      180
aggcctggac agggtctgga gtggattgga tacattaatc ctagcagtgg ttatactaac      240
tacaatcaga gttcaagga caaggccaca ttgactgcag acaaatcctc cagcacagcc      300
tacatgcaac tgagcagcct gacatctgag gactctgcag tctattactg tgcaagagat      360
ggtaactatg accactggta cttcgatgtc tggggcacag gaccacggt caccgtctcc       420
tcaggtggag gtggatcagg tggaggtgga tctggtggag gtggatctga cattgtgatg      480
tcacagtctc catcctccct ggctgtgtca gcaggagaga gggtcactat gagctgcaga      540
tccagtcaga gtctgctcaa cagtagaacc cgaaagaact acttggcttg gtaccagcag      600
aaaccagggc agtctcctaa gctgctgatc tactgggcat ccactaggga atctggggtc      660
cctgatcgct tctcaggcag tggatctggg acagatttca ctctcaccat cagcagtgtg      720
caggctgaag acctggcagt ttattactgc gagcaatctt ataatctatt cacgttcggc      780
tcggggacaa agttggaaat aaaacgg                                           807
```

<210> SEQ ID NO 58
<211> LENGTH: 786
<212> TYPE: DNA
<213> ORGANISM: Artificial Sequence
<220> FEATURE:
<223> OTHER INFORMATION: Synthetic Construct

<400> SEQUENCE: 58

```
atggccctcc cggtaacggc tctgctgctt ccactcgcac tgctcttgca tgctgccaga      60
ccacaggttc aactgcagca gcctggggct gagctggtga ggcctggggc ttcagtgaag      120
atgtcctgca aggcttctgg ctacaccctc accactact tgatggactg gtaaaacag       180
aggcttggac aaggctttga gtggattgga aatattaatc ctaatagtgg tagtagtaac      240
tacaatgaga gttcaaggg caaggccaag ctgactgtag acaaatcctc cagcacagcc      300
tacatgcaac tcagcagcct gacatctgag gactctgcgg tctattactg tgcaatacgg      360
cactatggtg gtagtctctt tgactactgg ggccaaggca ccactctcac agtctcctca      420
ggtggaggtg gatcaggtgg aggtggatct ggtggaggtg gatctgacat caagatgacc      480
cagtctccat cttccatgta tgcatctcta ggagagagag tcactatcac ttgcaaggcg      540
agtcaggaca ttaatagcta tttaagctgg ttccagcaga accagggaa atctcctaag       600
accctgatct atcgtgcaaa cagattggta gatggggtcc catcaaggtt cagtggcagt      660
ggatctgggc aagattattc tctcaccatc agcagcctgg agtatgaaga tatgggaatt      720
tattattgtc tacagtatga tgagttgctc acgttcggtg ctgggaccaa gctggagctg      780
aaacgg                                                                  786
```

<210> SEQ ID NO 59
<211> LENGTH: 804
<212> TYPE: DNA
<213> ORGANISM: Artificial Sequence
<220> FEATURE:
<223> OTHER INFORMATION: Synthetic Construct

```
<400> SEQUENCE: 59
atggccctcc cggtaacggc tctgctgctt ccactcgcac tgctcttgca tgctgccaga      60
ccacaggttc aactgcagca gcctggggct gagctggtga ggcctggggc ttcagtgaag     120
atgtcctgca aggcttctgg ctacaccctc accacctact tgatggactg ggtaaaacag     180
aggcttggac aaggctttga gtggattgga aatattaatc ctaatagtgg tagtagtaac     240
tacaatgaga agttcaaggg caaggccaag ctgactgtag acaaatcctc cagcacagcc     300
tacatgcaac tcagcagcct gacatctgag gactctgcgg tctattactg tgcaatacgg     360
cactatggtg gtagtctctt tgactactgg ggccaaggca ccactctcac agtctcctca     420
ggtggaggtg gatcaggtgg aggtggatct ggtggaggtg gatctgacat tgtgatgtca     480
cagtctccat cctccctggc tgtgtcagca ggagagaggg tcactatgag ctgcagatcc     540
agtcagagtc tgctcaacag tagaacccga aagaactact ggcttggta ccagcagaaa      600 ccagggcagt ctcctaagct gctgatctac tgggcatcca ctaggaatc tggggtccct      660 gatcgcttct caggcagtgg atctgggaca gatttcactc tcaccatcag cagtgtgcag     720
gctgaagacc tggcagttta ttactgcgag caatcttata atctattcac gttcggctcg     780
gggacaaagt tggaaataaa acgg                                            804

<210> SEQ ID NO 60
<211> LENGTH: 15
<212> TYPE: PRT
<213> ORGANISM: Artificial Sequence
<220> FEATURE:
<223> OTHER INFORMATION: Synthetic Construct

<400> SEQUENCE: 60

Gly Gly Gly Gly Ser Gly Gly Gly Gly Ser Gly Gly Gly Gly Ser
1               5                   10                  15
```

RECOMBINANT CD123-BINDING ANTIBODIES

CROSS-REFERENCE TO RELATED APPLICATIONS

This application is a National Stage of International Application No. PCT/US2018/042709, filed Jul. 20, 2018, which claims benefit of U.S. Provisional Application No. 62/534,957, filed Jul. 20, 2017, which is hereby incorporated herein by reference in its entirety.

BACKGROUND

Surgery, radiation therapy, and chemotherapy have been the standard accepted approaches for treatment of cancers including leukemia, solid tumors, and metastases. Immunotherapy (sometimes called biological therapy, biotherapy, or biological response modifier therapy), which uses the body's immune system, either directly or indirectly, to shrink or eradicate cancer has been studied for many years as an adjunct to conventional cancer therapy. It is believed that the human immune system is an untapped resource for cancer therapy and that effective treatment can be developed once the components of the immune system are properly harnessed.

SUMMARY

Compositions and methods for targeted treatment of CD123-expressing cancers are disclosed. For example, anti-CD123 antibodies are disclosed herein that are capable of selectively binding CD123-expressing cancers. Therefore, recombinant antibodies and other proteins comprising the antigen binding regions from these antibodies are also disclosed. In particular, anti-CD123 monoclonal antibodies from hybridomas 3F5, 4E10, 12H5, 15A12, 17E7, and 12H11 are provided herein. Also disclosed are recombinant, humanized, and/or chimeric antibodies comprising at least the antigen binding regions of one or more of these antibodies.

Also disclosed are multispecific, multivalent antibodies that are able to engage T-cells to destroy CD123-expressing malignant cells. The antibodies can be engineered from fusion polypeptides, such as fusion polypeptides having the following formula:

$V_LI-V_HI-V_LT-V_HT$, $V_LT-V_HT-V_LI-V_HI$, $V_HT-V_LT-V_HI-V_LI$, $V_HI-V_LI-V_HT-V_LT$, $V_LI-V_HI-V_HT-V_LT$, $V_LT-V_HT-V_HI-V_LI$, wherein "$V_LI$" is a light chain variable domain specific for an immune cell antigen;
wherein "$V_HT$" is a heavy chain variable domain specific for CD123;
wherein "$V_LT$" is a light chain variable domain specific for CD123;
wherein "$V_HI$" is a heavy chain variable domain specific for the immune cell antigen; and
wherein "-" consists of a peptide linker or a peptide bond.

The immune cell antigen can be a cell surface molecule that is expressed on human NK cells, T cells, monocytes, macrophages or granulocytes. For example, the cell surface molecule can be antigen CD2, CD3, CD16, CD64, CD89; NKp30, NKp44, NKp46, NKp80 (KLR-F1), NKG2C or NKG2D.

Also disclosed is an isolated nucleic acid encoding the disclosed fusion polypeptide, as well as nucleic acid vectors containing this isolated nucleic acid operably linked to an expression control sequence. Also disclosed are cells transfected with these vectors and the use of these cells to produce the disclosed fusion polypeptides.

Also disclosed is a pharmaceutical composition comprising a molecule disclosed herein in a pharmaceutically acceptable carrier. Also disclosed is a method for treating cancer in a subject that involves administering to the subject a therapeutically effective amount of a disclosed pharmaceutical composition. In some cases, the cancer can be any CD123-expressing malignancy. In some cases, the cancer comprises Acute Myeloid Leukemia (AML), blastic plasmocytoid dendritic cell neoplasm, hairy cell leukemia, or Acute Lymphoblastic Leukemia.

In some embodiments, the anti-CD123 scFv is derived from hybridoma 3F5, 4E10, 12H5, 15A12, 17E7, 12H11, or combinations thereof. In some embodiments, the anti-CD123 scFv can comprise a variable heavy ($V_H$) domain having CDR1, CDR2 and CDR3 sequences and a variable light ($V_L$) domain having CDR1, CDR2 and CDR3 sequences.

For example, in some embodiments, the CDR1 sequence of the $V_H$ domain comprises the amino acid sequence GYTFTDYN (SEQ ID NO:1), CDR2 sequence of the $V_H$ domain comprises the amino acid sequence INPNNGGT (SEQ ID NO:2), CDR3 sequence of the $V_H$ domain comprises the amino acid sequence ARKGYGGNYDYFDY (SEQ ID NO:3), CDR1 sequence of the $V_L$ comprises the amino acid sequence QSIGTS (SEQ ID NO:4), CDR2 sequence of the $V_L$ domain comprises the amino acid sequence YASx (SEQ ID NO:5), and CDR3 sequence of the $V_L$ domain comprises the amino acid sequence QQSNSWPYT (SEQ ID NO:6).

In some embodiments, the CDR1 sequence of the $V_H$ domain comprises the amino acid sequence GFNIKDTY (SEQ ID NO:7) or GFSLSTYGMG (SEQ ID NO:8), the CDR2 sequence of the $V_H$ domain comprises the amino acid sequence IDPANGNT (SEQ ID NO:9) or IYWDDDK (SEQ ID NO:10), the CDR3 sequence of the $V_H$ domain comprises the amino acid sequence ALYYYGGSLDY (SEQ ID NO:11) or AQSLIYDGYYGFAY (SEQ ID NO:12), the CDR1 sequence of the $V_L$ comprises the amino acid sequence QSLLYSGNQKNY (SEQ ID NO:13), the CDR2 sequence of the $V_L$ domain comprises the amino acid sequence WASx (SEQ ID NO:14), and the CDR3 sequence of the $V_L$ domain comprises the amino acid sequence QQYYSYPRT (SEQ ID NO:15).

In some embodiments, the CDR1 sequence of the $V_H$ domain comprises the amino acid sequence GYTFTYYG (SEQ ID NO:16), the CDR2 sequence of the $V_H$ domain comprises the amino acid sequence INTYSGVP (SEQ ID NO:17), the CDR3 sequence of the $V_H$ domain comprises the amino acid sequence ARWIYYSDLYGMDY (SEQ ID NO:18), the CDR1 sequence of the $V_L$ comprises the amino acid sequence QSIVHSNGDTY (SEQ ID NO:19), the CDR2 sequence of the $V_L$ domain comprises the amino acid sequence KVSx (SEQ ID NO:20), and the CDR3 sequence of the $V_L$ domain comprises the amino acid sequence FQGSHVPWT (SEQ ID NO:21).

In some embodiments, the CDR1 sequence of the $V_H$ domain comprises the amino acid sequence GYTFSSYW (SEQ ID NO:22) or GYTLTTYL (SEQ ID NO:23), the CDR2 sequence of the $V_H$ domain comprises the amino acid sequence INPSSGYT (SEQ ID NO:24) or INPNSGSS (SEQ ID NO:25), the CDR3 sequence of the $V_H$ domain comprises the amino acid sequence ARDGNYDHWYFDV (SEQ ID NO:26) or AIRHYGGSLFDY (SEQ ID NO:27), the CDR1 sequence of the $V_L$ comprises the amino acid sequence QDINSY (SEQ ID NO:28) or QSLLNSRTRKNY (SEQ ID NO:29), the CDR2 sequence of the $V_L$ domain comprises the amino acid sequence WASx (SEQ ID NO:14), or RANx (SEQ ID NO:30), and the CDR3 sequence of the $V_L$ domain comprises the amino acid sequence LQYDELLT (SEQ ID NO:31) or EQSYNLFT (SEQ ID NO:32).

In some embodiments, the some embodiments, the CDR1 sequence of the $V_H$ domain comprises the amino acid sequence GYTFTDYN (SEQ ID NO:1), GFNIKDTY (SEQ ID NO:7), GFSLSTYGMG (SEQ ID NO:8), GYTFTYYG (SEQ ID NO:16), GYTFSSYW (SEQ ID NO:22), or GYTLTTYL (SEQ ID NO:23); the CDR2 sequence of the $V_H$ domain comprises the amino acid sequence INPNNGGT (SEQ ID NO:2), IDPANGNT (SEQ ID NO:9), IYWDDDK (SEQ ID NO:10), INTYSGVP (SEQ ID NO:17), INPSSGYT (SEQ ID NO:24), or INPNSGSS (SEQ ID NO:25); the CDR3 sequence of the $V_H$ domain comprises the amino acid sequence ARKGYGGNYDYFDY (SEQ ID NO:3), ALYYYGGSLDY (SEQ ID NO:11), AQSLIYDGYYGFAY (SEQ ID NO:12), ARWIYYSD-LYGMDY (SEQ ID NO:18), ARDGNYDHWYFDV (SEQ ID NO:26), or AIRHYGGSLFDY (SEQ ID NO:27); the CDR1 sequence of the $V_L$ comprises the amino acid sequence QSIGTS (SEQ ID NO:4), QSLLYSGNQKNY (SEQ ID NO:13), QSIVHSNGDTY (SEQ ID NO:19), QDINSY (SEQ ID NO:28), or QSLLNSRTRKNY (SEQ ID NO:29); the CDR2 sequence of the $V_L$ domain comprises the amino acid sequence YAS (SEQ ID NO:5), WAS (SEQ ID NO:14), KVS (SEQ ID NO:20), or RAN (SEQ ID NO:30); the CDR3 sequence of the $V_L$ domain comprises the amino acid sequence QQSNSWPYT (SEQ ID NO:6), QQYYSY-PRT (SEQ ID NO:15), FQGSHVPWT (SEQ ID NO:21), LQYDELLT (SEQ ID NO:31), or EQSYNLFT (SEQ ID NO:32); or any combination thereof.

Therefore, in some embodiments, the anti-CD123 scFv $V_H$ domain comprises the amino acid sequence sequence

```
                            (SEQ ID NO: 33, 3F5HC1)
EVQLQQSGPELVKPGSSVKISCKASGYTFTDYNMDWVKQSHGKSLEWIGT

INPNNGGTSYNQKFKGKATLTVDKSSSTAYMELRSLTSEDSAVYYCARKG

YGGNYDYFDYWGQGTTLTVSS, (SEQ ID NO: 34, 12H1HC1)
EVQLQQSGAELVKPGASVKLSCTASGFNIKDTYMHWVKQRPEQGLEWIGR

IDPANGNTIYASKFQGKATITADTSSNTAYMQLSSLTSGDTAVYYCALYY

YGGSLDYWGQGTTLTVSS, (SEQ ID NO: 35, 12H1HC2)
QVTLKESGPGILQPSQTLSLTCSFSGFSLSTYGMGVSWIRQPSGKGLEWL

AHIYWDDDKRYNPSLKSRLTISKDTSNNQVFLKITSVDTADTATYYCAQS

LIYDGYYGFAYWGQGTLVTVSA, (SEQ ID NO: 36, 12H2HC1)
QIQLVQSGPELKKPGETVKISCKASGYTFTYYGMNWVKQAPGKGLEWMGW

INTYSGVPTYADDFKGRFAFSLETSVSTAYLQINNLKNEDTATYFCARWI

YYSDLYGMDYWGQGTSVTVSS,
```

```
                            (SEQ ID NO: 37, 15A12HC1)
QVQLQQSGAELAKPGASVKMSCKASGYTFSSYWMHWLKQRPGQGLEWIGY

INPSSGYTNYNQKFKDKATLTADKSSSTAYMQLSSLTSEDSAVYYCARDG

NYDHWYFDVWGTGTTVTVSS,
or (SEQ ID NO: 38, 15A12H02)
QVQLQQPGAELVRPGASVKMSCKASGYTLTTYLMDWVKQRLGQGFEWIGN

INPNSGSSNYNEKFKGKAKLTVDKSSSTAYMQLSSLTSEDSAVYYCAIRH

YGGSLFDYWGQGTTLTVSS.
```

In some embodiments, the anti-CD123 scFv $V_L$ domain comprises the amino acid sequence:

```
                            (SEQ ID NO: 39, 3F5LC1)
DILLTQSPAILSVSPGERVSFSCRASQSIGTSIHWYQQRTNGSPRLLIKY

ASESISGIPSRFSGSGSGTDFTLSINSVESEDIADYYCQQSNSWPYTFGG

GTKLEIK, (SEQ ID NO: 40, 12H1LC1)
DIVMSQSPSSLAVSVGERVTMSCKSSQSLLYSGNQKNYLAWYQQKPGQSP

KLLIYWASTRESGVPDRFTGSGSGTDFTLTISSVKAEDLAVYYCQQYYSY

PRTFGGGTKLEIK, (SEQ ID NO: 41, 12H2LC)
DVLMTQSPLSLPVSLGDQASISCRSSQSIVHSNGDTYLEWYLQKPGQSPK

LLIYKVSNRFSGVPDRFSGSGSGTDFTLKISRVEAEDLGVYHCFQGSHVP

WTFGGGTKLEIK, (SEQ ID NO: 42, 15A12LC1)
DIKMTQSPSSMYASLGERVTITCKASQDINSYLSWFQQKPGKSPKTLIYR

ANRLVDGVPSRFSGSGSGQDYSLTISSLEYEDMGIYYCLQYDELLTFGAG

TKLELK,
or (SEQ ID NO: 43, 15A12LC2)
DIVMSQSPSSLAVSAGERVTMSCRSSQSLLNSRTRKNYLAWYQQKPGQSP

KLLIYWASTRESGVPDRFSGSGSGTDFTLTISSVQAEDLAVYYCEQSYNL

FTFGSGTKLEIK.
```

The heavy and light chains are preferably separated by a linker. Suitable linkers for scFv antibodies are known in the art. In some embodiments, the linker comprises the amino acid sequence GGGGSGGGGSGGGGS (SEQ ID NO:60).

In some embodiments, the anti-CD123 scFv comprises an amino acid sequence:

```
                            (SEQ ID NO: 44 3F5HC1_LC)
EVQLQQSGPELVKPGSSVKISCKASGYTFTDYNMDWVKQSHGKSLEWIGT

INPNNGGTSYNQKFKGKATLTVDKSSSTAYMELRSLTSEDSAVYYCARKG

YGGNYDYFDYWGQGTTLTVSSGGGGSGGGGSGGGGSDILLTQSPAILSVS

PGERVSFSCRASQSIGTSIHWYQQRTNGSPRLLIKYASESISGIPSRFSG

SGSGTDFTLSINSVESEDIADYYCQQSNSWPYTFGGGTKLEIK.
```

In some embodiments, the anti-CD123 scFv comprises an amino acid sequence:

(SEQ ID NO: 45, 12H1HC1_LC1)
EVQLQQSGAELVKPGASVKLSCTASGFNIKDTYMHWVKQRPEQGLEWIGR
IDPANGNTIYASKFQGKATITADTSSNTAYMQLSSLTSGDTAVYYCALYY
YGGSLDYWGQGTTLTVSSGGGGSGGGGSGGGGSDIVMSQSPSSLAVSVGE
RVTMSCKSSQSLLYSGNQKNYLAWYQQKPGQSPKLLIYWASTRESGVPDR
FTGSGSGTDFTLTISSVKAEDLAVYYCQQYYSYPRTFGGGTKLEIK.

In some embodiments, the anti-CD123 scFv comprises an amino acid sequence:

(SEQ ID NO: 46, 12H1HC2_LC1)
QVTLKESGPGILQPSQTLSLTCSFSGFSLSTYGMGVSWIRQPSGKGLEWL
AHIYWDDDKRYNPSLKSRLTISKDTSNNQVFLKITSVDTADTATYYCAQS
LIYDGYYGFAYWGQGTLVTVSAGGGGSGGGGSGGGGSDIVMSQSPSSLAV
SVGERVTMSCKSSQSLLYSGNQKNYLAWYQQKPGQSPKLLIYWASTRESG
VPDRFTGSGSGTDFTLTISSVKAEDLAVYYCQQYYSYPRTFGGGTKLEIK.

In some embodiments, the anti-CD123 scFv comprises an amino acid sequence:

(SEQ ID NO: 47, 12H2HC1_LC1)
QIQLVQSGPELKKPGETVKISCKASGYTFTYYGMNWVKQAPGKGLEWMGW
INTYSGVPTYADDFKGRFAFSLETSVSTAYLQINNLKNEDTATYFCARWI
YYSDLYGMDYWGQGTSVTVSSGGGGSGGGGSGGGGSDVLMTQSPLSLPVS
LGDQASISCRSSQSIVHSNGDTYLEWYLQKPGQSPKLLIYKVSNRFSGVP
DRFSGSGSGTDFTLKISRVEAEDLGVYHCFQGSHVPWTFGGGTKLEIK.

In some embodiments, the anti-CD123 scFv comprises an amino acid sequence:

(SEQ ID NO: 48, 15A12HC1_LC1)
QVQLQQSGAELAKPGASVKMSCKASGYTFSSYWMHWLKQRPGQGLEWIGY
INPSSGYTNYNQKFKDKATLTADKSSTAYMQLSSLTSEDSAVYYCARDG
NYDHWYFDVWGTGTTVTVSSGGGGSGGGGSGGGGSDIKMTQSPSSMYASL
GERVTITCKASQDINSYLSWFQQKPGKSPKTLIYRANRLVDGVPSRFSGS
GSGQDYSLTISSLEYEDMGIYYCLQYDELLTFGAGTKLELK.

In some embodiments, the anti-CD123 scFv comprises an amino acid sequence:

(SEQ ID NO: 49, 15A12HC1_LC2)
QVQLQQSGAELAKPGASVKMSCKASGYTFSSYWMHWLKQRPGQGLEWIGY
INPSSGYTNYNQKFKDKATLTADKSSTAYMQLSSLTSEDSAVYYCARDG
NYDHWYFDVWGTGTTVTVSSGGGGSGGGGSGGGGSDIVMSQSPSSLAVSA
GERVTMSCRSSQSLLNSRTRKNYLAWYQQKPGQSPKLLIYWASTRESGVP
DRFSGSGSGTDFTLTISSVQAEDLAVYYCEQSYNLFTFGSGTKLEIK.

In some embodiments, the anti-CD123 scFv comprises an amino acid sequence:

(SEQ ID NO: 50, 15A12HC2_LC1)
QVQLQQPGAELVRPGASVKMSCKASGYTLTTYLMDWVKQRLGQGFEWIGN
INPNSGSSNYNEKFKGKAKLTVDKSSSTAYMQLSSLTSEDSAVYYCAIRH
YGGSLFDYWGQGTTLTVSSGGGGSGGGGSGGGGSDIKMTQSPSSMYASLG
ERVTITCKASQDINSYLSWFQQKPGKSPKTLIYRANRLVDGVPSRFSGSG
SGQDYSLTISSLEYEDMGIYYCLQYDELLTFGAGTKLELK.

In some embodiments, the anti-CD123 scFv comprises an amino acid sequence:

(SEQ ID NO: 51, 15A12HC2_LC2)
QVQLQQPGAELVRPGASVKMSCKASGYTLTTYLMDWVKQRLGQGFEWIGN
INPNSGSSNYNEKFKGKAKLTVDKSSSTAYMQLSSLTSEDSAVYYCAIRH
YGGSLFDYWGQGTTLTVSSGGGGSGGGGSGGGGSDIVMSQSPSSLAVSAG
ERVTMSCRSSQSLLNSRTRKNYLAWYQQKPGQSPKLLIYWASTRESGVPD
RFSGSGSGTDFTLTISSVQAEDLAVYYCEQSYNLFTFGSGTKLEIK.

In some embodiments, the anti-CD123 scFv is encoded by the nucleic acid sequence:

(SEQ ID NO: 52, 3F5HC1_LC)
ATGGCCCTCCCGGTAACGGCTCTGCTGCTTCCACTCGCACTGCTCTTGCA
TGCTGCCAGACCAGAGGTCCAGCTGCAACAGTCTGGACCTGAGCTGGTGA
AGCCTGGGTCTTCAGTGAAGATATCCTGCAAAGCTTCTGGATACACATTC
ACTGACTACAACATGGACTGGGTGAAGCAGAGTCATGGAAAGAGCCTTGA
GTGGATTGGAACTATTAATCCTAACAATGGTGGTACTAGCTACAACCAGA
AGTTCAAGGGCAAGGCCACATTGACTGTAGACAAGTCCTCCAGCACAGCC
TACATGGAGCTCCGCAGCCTGACATCTGAAGACTCTGCAGTCTATTACTG
TGCAAGAAAGGGCTATGGTGGTAACTACGACTACTTTGACTACTGGGGCC
AAGGCACCACTCTCACAGTCTCCTCAGGTGGAGGTGGATCAGGTGGAGGT
GGATCTGGTGGAGGTGGATCTGACATCTTGCTGACTCAGTCTCCAGCCAT
CCTGTCTGTGAGTCCAGGAGAAAGAGTCAGTTTCTCCTGCAGGGCCAGTC
AGAGCATTGGCACAAGCATACACTGGTATCAGCAAAGAACAAATGGTTCT
CCAAGGCTTCTCATAAAGTATGCTTCTGAGTCTATCTCTGGGTTCCCTTC
CAGGTTTAGTGGCAGTGGATCAGGGACAGATTTTACTCTTAGCATCAACA
GTGTGGAGTCTGAAGATATTGCAGATTATTACTGTCAACAAAGTAATAGC
TGGCCGTACACGTTCGGAGGGGGGACCAAGCTGGAAATAAAACGG.

In some embodiments, the anti-CD123 scFv is encoded by the nucleic acid sequence:

(SEQ ID NO: 53, 12H1HC1_LC1)
ATGGCCCTCCCGGTAACGGCTCTGCTGCTTCCACTCGCACTGCTCTTGCA
TGCTGCCAGACCAGAGGTTCAGCTGCAGCAGTCTGGGGCAGAGCTTGTGA
AGCCAGGGGCCTCAGTCAAGTTGTCCTGCACAGCTTCTGGCTTCAACATT
AAAGACACCTATATGCACTGGGTGAAGCAGAGGCCTGAACAGGGCCTGGA

-continued
GTGGATTGGAAGGATTGATCCTGCGAATGGTAATACTATATATGCCTCAA

AGTTCCAGGGCAAGGCCACTATAACAGCAGACACATCATCCAACACAGCC

TACATGCAGCTCAGCAGCCTGACATCTGGGGACACTGCCGTCTATTACTG

TGCTCTTTATTACTATGGTGGTAGCCTTGACTACTGGGGCCAAGGCACCA

CTCTCACAGTCTCCTCAGGTGGAGGTGGATCAGGTGGAGGTGGATCTGGT

GGAGGTGGATCTGACATTGTGATGTCACAGTCTCCATCCTCCCTAGCTGT

GTCAGTTGGAGAGAGGGTTACTATGAGCTGCAAGTCCAGTCAGAGCCTTT

TATATAGTGGCAATCAAAAGAACTACTTGGCCTGGTACCAGCAGAAACCA

GGGCAGTCTCCTAAACTGCTGATTTACTGGGCATCCACTAGGGAATCTGG

GGTCCCTGATCGCTTCACAGGCAGTGGATCTGGGACAGATTTCACTCTCA

CCATCAGCAGTGTGAAGGCTGAAGACCTGGCAGTTTATTACTGTCAGCAA

TATTATAGCTATCCTCGGACGTTCGGTGGAGGCACCAAGCTGGAAATCAA

ACGG.

In some embodiments, the anti-CD123 scFv is encoded by the nucleic acid sequence:

(SEQ ID NO: 54, 12H1HC1_LC2)
ATGGCCCTCCCGGTAACGGCTCTGCTGCTTCCACTCGCACTGCTCTTGCA

TGCTGCCAGACCACAGGTTACTCTGAAAGAGTCTGGCCCTGGGATATTGC

AGCCCTCCCAGACCCTCAGTCTGACTTGTTCTTTCTCTGGGTTTTCACTG

AGCACTTATGGTATGGGTGTGAGCTGGATTCGTCAGCCTTCAGGAAAGGG

TCTGGAGTGGCTGGCACACATTTACTGGGATGATGACAAGCGCTATAACC

CATCCCTGAAGAGCCGGCTCACAATCTCCAAGGATACCTCCAACAACCAG

GTATTCCTCAAGATCACCAGTGTGGACACTGCAGATACTGCCACATACTA

CTGTGCTCAAAGCCTGATCTATGATGGTTACTACGGGTTTGCCTACTGGG

GCCAAGGGACTCTGGTCACTGTCTCTGCAGGTGGAGGTGGATCAGGTGGA

GGTGGATCTGGTGGAGGTGGATCTGACATTGTGATGTCACAGTCTCCATC

CTCCCTAGCTGTGTCAGTTGGAGAGAGGGTTACTATGAGCTGCAAGTCCA

GTCAGAGCCTTTTATATAGTGGCAATCAAAAGAACTACTTGGCCTGGTAC

CAGCAGAAACCAGGGCAGTCTCCTAAACTGCTGATTTACTGGGCATCCAC

TAGGGAATCTGGGGTCCCTGATCGCTTCACAGGCAGTGGATCTGGGACAG

ATTTCACTCTCACCATCAGCAGTGTGAAGGCTGAAGACCTGGCAGTTTAT

TACTGTCAGCAATATTATAGCTATCCTCGGACGTTCGGTGGAGGCACCAA

GCTGGAAATCAAACGG.

In some embodiments, the anti-CD123 scFv is encoded by the nucleic acid sequence:

(SEQ ID NO: 55, 12H2HC1_LC1)
ATGGCCCTCCCGGTAACGGCTCTGCTGCTTCCACTCGCACTGCTCTTGCA

TGCTGCCAGACCACAGATCCAGTTGGTGCAATCTGGACCTGAGCTGAAGA

AGCCTGGAGAGACAGTCAAGATCTCCTGCAAGGCTTCTGGGTATACCTTC

ACATACTATGGAATGAACTGGGTGAAGCAGGCTCCAGGAAAGGGTTTAGA

GTGGATGGGCTGGATAAACACCTACTCTGGAGTGCCAACATATGCTGATG

ACTTCAAGGGACGGTTTGCCTTCTCTTTGGAAACCTCTGTCAGCACTGCC

TATTTGCAGATCAACAACCTCAAAAATGAGGACACGGCTACATATTTTTG

TGCAAGATGGATCTACTATAGTGACCTCTATGGTATGGACTACTGGGGTC

AAGGAACCTCAGTCACCGTCTCCTCAGGTGGAGGTGGATCAGGTGGAGGT

GGATCTGGTGGAGGTGGATCTGATGTTTTGATGACCCAAAGTCCACTCTC

CCTGCCTGTCAGTCTTGGAGATCAAGCCTCCATCTCTTGTAGATCTAGTC

AGAGTATTGTACATAGTAATGGAGACACGTATTTAGAATGGTATTTGCAG

AAACCAGGCCAGTCTCCAAAGCTCCTGATCTACAAAGTTTCTAACCGATT

TTCTGGGGTCCCAGACAGGTTCAGTGGCAGTGGATCAGGGACAGATTTCA

CACTCAAGATCAGCAGAGTGGAGGCTGAGGATCTGGGAGTTTATCACTGC

TTTCAAGGTTCACATGTTCCGTGGACGTTCGGTGGAGGCACCAAGCTGGA

AATCAAACGG.

In some embodiments, the anti-CD123 scFv is encoded by the nucleic acid sequence:

(SEQ ID NO: 56, 15A12HC1_LC1)
ATGGCCCTCCCGGTAACGGCTCTGCTGCTTCCACTCGCACTGCTCTTGCA

TGCTGCCAGACCACAGGTCCAGCTGCAGCAGTCTGGGGCTGAACTGGCAA

AACCTGGGGCCTCAGTGAAGATGTCCTGCAAGGCTTCTGGCTACACCTTT

TCTAGCTACTGGATGCACTGGCTAAAACAGAGGCCTGGACAGGGTCTGGA

GTGGATTGGATACATTAATCCTAGCAGTGGTTATACTAACTACAATCAGA

AGTTCAAGGACAAGGCCACATTGACTGCAGACAAATCCTCCAGCACAGCC

TACATGCAACTGAGCAGCCTGACATCTGAGGACTCTGCAGTCTATTACTG

TGCAAGAGATGGTAACTATGACCACTGGTACTTCGATGTCTGGGGCACAG

GGACCACGGTCACCGTCTCCTCAGGTGGAGGTGGATCAGGTGGAGGTGGA

TCTGGTGGAGGTGGATCTGACATCAAGATGACCCAGTCTCCATCTTCCAT

GTATGCATCTCTAGGAGAGAGTCACTATCACTTGCAAGGCGAGTCAGG

ACATTAATAGCTATTTAAGCTGGTTCCAGCAGAAACCAGGGAAATCTCCT

AAGACCCTGATCTATCGTGCAAACAGATTGGTAGATGGGGTCCCATCAAG

GTTCAGTGGCAGTGGATCTGGGCAAGATTATTCTCTCACCATCAGCAGCC

TGGAGTATGAAGATATGGGAATTTATTATTGTCTACAGTATGATGAGTTG

CTCACGTTCGGTGCTGGGACCAAGCTGGAGCTGAAACGG.

In some embodiments, the anti-CD123 scFv is encoded by the nucleic acid sequence:

(SEQ ID NO: 57, 15A12HC1_LC2)
ATGGCCCTCCCGGTAACGGCTCTGCTGCTTCCACTCGCACTGCTCTTGCA

TGCTGCCAGACCACAGGTCCAGCTGCAGCAGTCTGGGGCTGAACTGGCAA

AACCTGGGGCCTCAGTGAAGATGTCCTGCAAGGCTTCTGGCTACACCTTT

TCTAGCTACTGGATGCACTGGCTAAAACAGAGGCCTGGACAGGGTCTGGA

GTGGATTGGATACATTAATCCTAGCAGTGGTTATACTAACTACAATCAGA

AGTTCAAGGACAAGGCCACATTGACTGCAGACAAATCCTCCAGCACAGCC

TACATGCAACTGAGCAGCCTGACATCTGAGGACTCTGCAGTCTATTACTG

-continued
TGCAAGAGATGGTAACTATGACCACTGGTACTTCGATGTCTGGGGCACAG

GGACCACGGTCACCGTCTCCTCAGGTGGAGGTGGATCAGGTGGAGGTGGA

TCTGGTGGAGGTGGATCTGACATTGTGATGTCACAGTCTCCATCCTCCCT

GGCTGTGTCAGCAGGAGAGAGGGTCACTATGAGCTGCAGATCCAGTCAGA

GTCTGCTCAACAGTAGAACCCGAAAGAACTACTTGGCTTGGTACCAGCAG

AAACCAGGGCAGTCTCCTAAGCTGCTGATCTACTGGGCATCCACTAGGGA

ATCTGGGGTCCCTGATCGCTTCTCAGGCAGTGGATCTGGGACAGATTTCA

CTCTCACCATCAGCAGTGTGCAGGCTGAAGACCTGGCAGTTTATTACTGC

GAGCAATCTTATAATCTATTCACGTTCGGCTCGGGGACAAAGTTGGAAAT

AAAACGG.

In some embodiments, the anti-CD123 scFv is encoded by the nucleic acid sequence:

```
                    (SEQ ID NO: 58, 15A12HC2_LC1)
ATGGCCCTCCCGGTAACGGCTCTGCTGCTTCCACTCGCACTGCTCTTGCA

TGCTGCCAGACCACAGGTTCAACTGCAGCAGCCTGGGGCTGAGCTGGTGA

GGCCTGGGGCTTCAGTGAAGATGTCCTGCAAGGCTTCTGGCTACACCCTC

ACCACCTACTTGATGGACTGGGTAAAACAGAGGCTTGGACAAGGCTTTGA

GTGGATTGGAAATATTAATCCTAATAGTGGTAGTAGTAACTACAATGAGA

AGTTCAAGGGCAAGGCCAAGCTGACTGTAGACAAATCCTCCAGCACAGCC

TACATGCAACTCAGCAGCCTGACATCTGAGGACTCTGCGGTCTATTACTG

TGCAATACGGCACTATGGTGGTAGTCTCTTTGACTACTGGGGCCAAGGCA

CCACTCTCACAGTCTCCTCAGGTGGAGGTGGATCAGGTGGAGGTGGATCT

GGTGGAGGTGGATCTGACATCAAGATGACCCAGTCTCCATCTTCCATGTA

TGCATCTCTAGGAGAGAGTCACTATCACTTGCAAGGCGAGTCAGGACA

TTAATAGCTATTTAAGCTGGTTCCAGCAGAAACCAGGGAAATCTCCTAAG

ACCCTGATCTATCGTGCAAACAGATTGGTAGATGGGGTCCCATCAAGGTT

CAGTGGCAGTGGATCTGGGCAAGATTATTCTCTCACCATCAGCAGCCTGG

AGTATGAAGATATGGGAATTTATTATTGTCTACAGTATGATGAGTTGCTC

ACGTTCGGTGCTGGGACCAAGCTGGAGCTGAAACGG.
```

In some embodiments, the anti-CD123 scFv is encoded by the nucleic acid sequence:

```
                    (SEQ ID NO: 59, 15A12HC2_LC2)
ATGGCCCTCCCGGTAACGGCTCTGCTGCTTCCACTCGCACTGCTCTTGCA

TGCTGCCAGACCACAGGTTCAACTGCAGCAGCCTGGGGCTGAGCTGGTGA

GGCCTGGGGCTTCAGTGAAGATGTCCTGCAAGGCTTCTGGCTACACCCTC

ACCACCTACTTGATGGACTGGGTAAAACAGAGGCTTGGACAAGGCTTTGA

GTGGATTGGAAATATTAATCCTAATAGTGGTAGTAGTAACTACAATGAGA

AGTTCAAGGGCAAGGCCAAGCTGACTGTAGACAAATCCTCCAGCACAGCC

TACATGCAACTCAGCAGCCTGACATCTGAGGACTCTGCGGTCTATTACTG

TGCAATACGGCACTATGGTGGTAGTCTCTTTGACTACTGGGGCCAAGGCA

CCACTCTCACAGTCTCCTCAGGTGGAGGTGGATCAGGTGGAGGTGGATCT

GGTGGAGGTGGATCTGACATTGTGATGTCACAGTCTCCATCCTCCCTGGC

TGTGTCAGCAGGAGAGAGGGTCACTATGAGCTGCAGATCCAGTCAGAGTC

TGCTCAACAGTAGAACCCGAAAGAACTACTTGGCTTGGTACCAGCAGAAA

CCAGGGCAGTCTCCTAAGCTGCTGATCTACTGGGCATCCACTAGGGAATC

TGGGGTCCCTGATCGCTTCTCAGGCAGTGGATCTGGGACAGATTTCACTC

TCACCATCAGCAGTGTGCAGGCTGAAGACCTGGCAGTTTATTACTGCGAG

CAATCTTATAATCTATTCACGTTCGGCTCGGGGACAAAGTTGGAAATAAA

ACGG.
```

Also disclosed are isolated nucleic acid sequences encoding the disclosed polypeptides, vectors comprising these isolated nucleic acids, and cells containing these vectors. For example, the cell can be an immune effector cell selected from the group consisting of an alpha-beta T cells, a gamma-delta T cell, a Natural Killer (NK) cells, a Natural Killer T (NKT) cell, a B cell, an innate lymphoid cell (ILC), a cytokine induced killer (CIK) cell, a cytotoxic T lymphocyte (CTL), a lymphokine activated killer (LAK) cell, and a regulatory T cell.

In some embodiments, the cell exhibits an anti-tumor immunity when the antibody binds to CD123.

Also disclosed is a method of providing an anti-tumor immunity in a subject with a CD123-expressing cancer that involves administering to the subject an effective amount of an immune effector cell genetically modified with a disclosed CD123-specific CAR.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
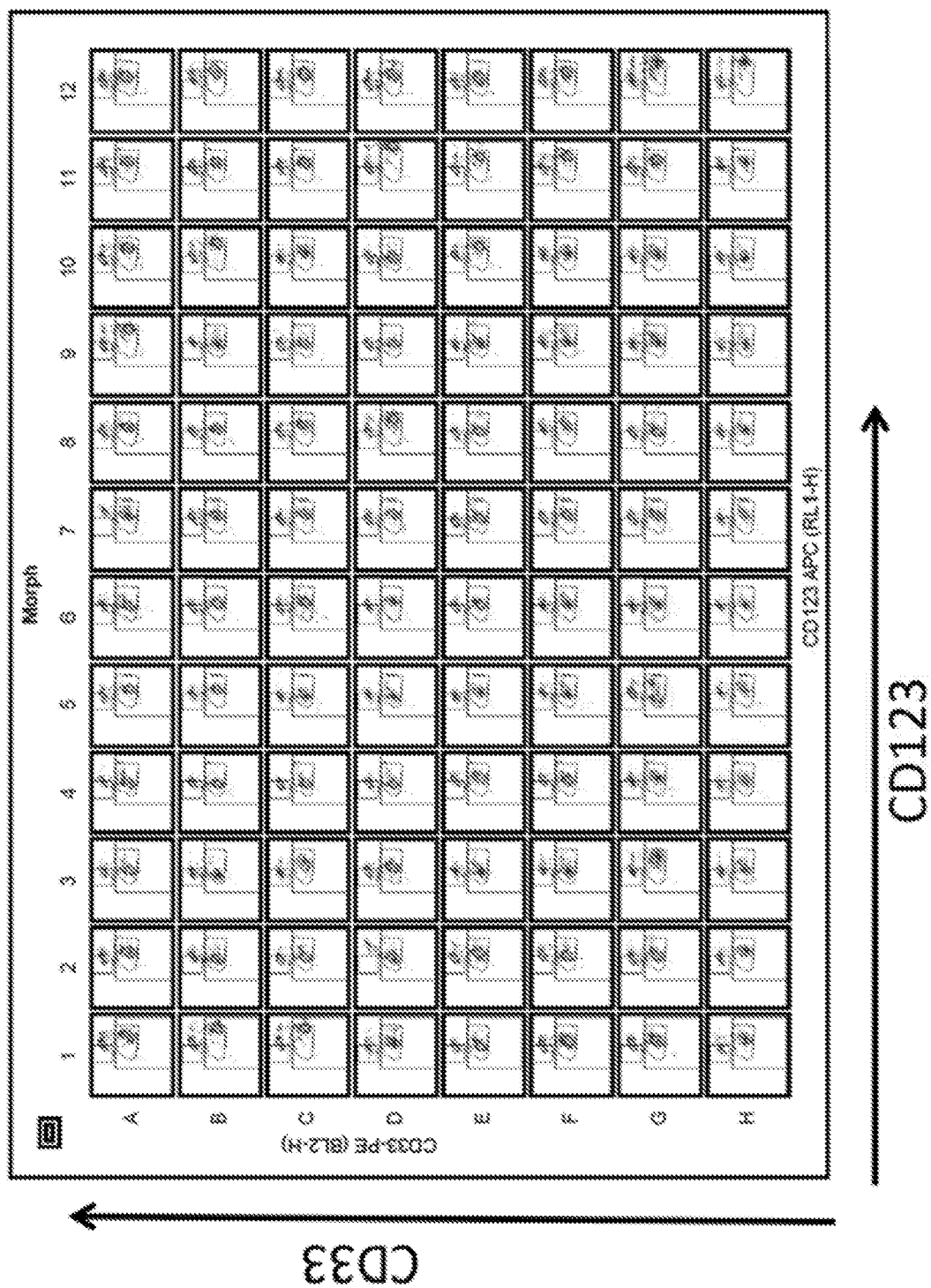
FIG. 1 shows results of primary screen for anti-CD123 antibodies.

Disclosed herein are antibodies that can specifically recognize tumor-associated antigens (TAA) on CD123-expressing cancers. Therefore, also disclosed are methods for providing an anti-tumor immunity in a subject with CD123-expressing cancers that involves treating the subject with the disclosed antibodies.

Antibodies

Antibodies that can be used in the disclosed compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. USA, 90:2551-255 (1993); Jakobovits et al., Nature, 362:255-258 (1993); Bruggemann et al., Year in Immuno., 7:33 (1993)). Human antibodies can also be produced in phage display libraries (Hoogenboom et al., J. Mol. Biol., 227:381 (1991); Marks et al., J. Mol. Biol., 222:581 (1991)). The techniques of Cote et al. and Boerner et al. are also available for the preparation of human monoclonal antibodies (Cole et al., Monoclonal Antibodies and Cancer Therapy, Alan R. Liss, p. 77 (1985); Boerner et al., J. Immunol., 147(1):86-95 (1991)).

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-327 (1988); and Presta, Curr. Op. Struct. Biol., 2:593-596 (1992))

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, a humanized form of a non human antibody (or a fragment thereof) is a chimeric antibody or fragment (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the non-modified antibody or antibody fragment.

Techniques can also be adapted for the production of single-chain antibodies specific to an antigenic protein of the present disclosure. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two $V_H$ and two $V_L$ regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

A bi-specific antibody designed to selectively bind CD3 and CD123 would trigger non-specific T-cell activation & cytokine storm. A bi-specific diabody designed to selectively bind CD3 and CD123 would have a molecular weight (55-60 kD) less than the renal clearance threshold, which would result in rapid elimination. As such, diabodies must be administered by a continuous infusion. The disclosed tetravalent, bi-specific antibody can have a molecular weight (e.g., 105-110 kD) greater than the renal filtration threshold with markedly extended PK.

Provided are fusion polypeptides capable of forming a multivalent engineered antibody that is able to engage T-cells to destroy CD123-expressing malignant cells. The engineered antibody may comprise for example, at least one scFv, at least one Fab fragment, at least one Fv fragment, etc. It may be bivalent, trivalent, tetravalent, etc. The multivalent antibodies is multispecific, e.g., bispecific, trispecific, tetraspecific, etc. The multivalent antibodies may be in any form, such as a diabody, triabody, tetrabody, etc.

Bivalent and bispecific antibodies can be constructed using only antibody variable domains. A fairly efficient and relatively simple method is to make the linker sequence between the $V_H$ and $V_L$ domains so short that they cannot fold over and bind one another. Reduction of the linker length to 3-12 residues prevents the monomeric configuration of the scFv molecule and favors intermolecular VH-VL pairings with formation of a 60 kDa non-covalent scFv dimer "diabody". The diabody format can also be used for generation of recombinant bis-pecific antibodies, which are obtained by the noncovalent association of two single-chain fusion products, consisting of the VH domain from one antibody connected by a short linker to the VL domain of another antibody. Reducing the linker length still further below three residues can result in the formation of trimers ("triabody", about 90 kDa) or tetramers ("tetrabody", about 120 kDa). For a review of engineered antibodies, particularly single domain fragments, see Holliger and Hudson, 2005, Nature Biotechnology, 23:1126-1136. All of such engineered antibodies may be used in the fusion polypeptides provided herein. Tetravalent Tandab® may be prepared substantially as described in WO 1999057150 A3 or US20060233787, which are incorporated by reference for the teaching of methods of making Tandab® molecules.

The antigen recognition sites or entire variable regions of the engineered antibodies may be derived from one or more parental antibodies directed against any antigen of interest (e.g., CD123). The parental antibodies can include naturally occurring antibodies or antibody fragments, antibodies or antibody fragments adapted from naturally occurring antibodies, antibodies constructed de novo using sequences of antibodies or antibody fragments known to be specific for an antigen of interest. Sequences that may be derived from parental antibodies include heavy and/or light chain variable regions and/or CDRs, framework regions or other portions thereof.

Multivalent, multispecific antibodies may contain a heavy chain comprising two or more variable regions and/or a light chain comprising one or more variable regions wherein at least two of the variable regions recognize different epitopes on the same antigen.

Candidate engineered antibodies for inclusion in the fusion polypeptides, or the fusion polypeptides themselves, may be screened for activity using a variety of known assays. For example, screening assays to determine binding specificity are well known and routinely practiced in the art. For a comprehensive discussion of such assays, see Harlow et al. (Eds.), ANTIBODIES: A LABORATORY MANUAL; Cold Spring Harbor Laboratory; Cold Spring Harbor, N.Y., 1988, Chapter 6.

In some embodiments, the anti-CD123 binding agent is single chain variable fragment (scFv) antibody. The affinity/specificity of an anti-CD123 scFv is driven in large part by specific sequences within complementarity determining regions (CDRs) in the heavy ($V_H$) and light ($V_L$) chain. Each $V_H$ and $V_L$ sequence will have three CDRs (CDR1, CDR2, CDR3).

In some embodiments, the anti-CD123 binding agent is derived from natural antibodies, such as monoclonal antibodies. In some cases, the antibody is human. In some cases, the antibody has undergone an alteration to render it less immunogenic when administered to humans. For example, the alteration comprises one or more techniques selected from the group consisting of chimerization, humanization, CDR-grafting, deimmunization, and mutation of framework amino acids to correspond to the closest human germline sequence.

Tumor antigens are proteins that are produced by tumor cells that elicit an immune response, particularly T-cell mediated immune responses. The additional antigen binding domain can be an antibody or a natural ligand of the tumor antigen. The selection of the additional antigen binding domain will depend on the particular type of cancer to be treated. Tumor antigens are well known in the art and include, for example, a glioma-associated antigen, carcinoembryonic antigen (CEA), EGFRvIII, IL-IIRa, IL-13Ra, EGFR, FAP, B7H3, Kit, CA LX, CS-1, MUC1, BCMA, bcr-abI, HER2, β-human chorionic gonadotropin, alphafetoprotein (AFP), ALK, CD19, CD123, cyclin BI, lectin-reactive AFP, Fos-related antigen 1, ADRB3, thyroglobulin, EphA2, RAGE-1, RUI, RU2, SSX2, AKAP-4, LCK, OY-TESI, PAX5, SART3, CLL-1, fucosyl GM1, GloboH, MN-CA IX, EPCAM, EVT6-AML, TGS5, human telomerase reverse transcriptase, plysialic acid, PLAC1, RUI, RU2 (AS), intestinal carboxyl esterase, lewisY, sLe, LY6K, mut hsp70-2, M-CSF, MYCN, RhoC, TRP-2, CYPIBI, BORIS, prostase, prostate-specific antigen (PSA), PAX3, PAP, NY-ESO-1, LAGE-Ia, LMP2, NCAM, p53, p53 mutant, Ras mutant, gplOO, prostein, OR51E2, PANX3, PSMA, PSCA, Her2/neu, hTERT, HMWMAA, HAVCR1, VEGFR2, PDGFR-beta, survivin and telomerase, legumain, HPV E6,E7, sperm protein 17, SSEA-4, tyrosinase, TARP, WT1, prostate-carcinoma tumor antigen-1 (PCTA-1), ML-IAP, MAGE, MAGE-A1,MAD-CT-1, MAD-CT-2, MelanA/MART 1, XAGE1 , ELF2M, ERG (TMPRSS2 ETS fusion gene), NA17, neutrophil elastase, sarcoma translocation breakpoints, NY-BR-1, ephnnB2, CD20, CD22, CD24, CD30, CD123, CD38, CD44v6, CD97, CD171, CD179a, androgen receptor, FAP, insulin growth factor (IGF)-I, IGFII, IGF-I receptor, GD2, o-acetyl-GD2, GD3, GM3, GPRC5D, GPR20, CXORF61, folate receptor (FRa), folate receptor beta, ROR1, Flt3, TAG72, TN Ag, Tie 2, TEM1, TEM7R, CLDN6, TSHR, UPK2, and mesothelin. In a preferred embodiment, the tumor antigen is selected from the group consisting of folate receptor (FRa), mesothelin, EGFRvIII, IL-13Ra, CD123, CD19, CD123, BCMA, GD2, CLL-1, CA-IX, MUCI, HER2, and any combination thereof.

Non-limiting examples of tumor antigens include the following: Differentiation antigens such as tyrosinase, TRP-1, TRP-2 and tumor-specific multilineage antigens such as MAGE-1, MAGE-3, BAGE, GAGE-1, GAGE-2, pi 5; over-expressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE- 5, MAGE-6, RAGE, NY-ESO, pl85erbB2, pl80erbB-3, c-met, nm-23H1, PSA, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCASI, SDCCAG1 6, TA-90\Mac-2 binding protein\cyclophilm C-associated protein, TAAL6, TAG72, TLP, TPS, GPC3, MUC16, LMP1, EBMA-1, BARF-1, CS1, CD319, HER1, B7H6, L1CAM, IL6, and MET.

Nucleic Acids and Vectors

Also disclosed are polynucleotides and polynucleotide vectors encoding the disclosed CD123-specific antibodies that allow expression of the CD123-specific antibodies in the cells.

Nucleic acid sequences encoding the disclosed antibodies, and regions thereof, can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Expression of nucleic acids encoding antibodies is typically achieved by operably linking a nucleic acid encoding the antibody polypeptide to a promoter, and incorporating the construct into an expression vector. Typical cloning vectors contain transcription and translation terminators, initiation sequences, and promoters useful for regulation of the expression of the desired nucleic acid sequence.

The disclosed nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. In some embodiments, the polynucleotide vectors are lentiviral or retroviral vectors.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, MND (myeloproliferative sarcoma virus) promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. The promoter can alternatively be an inducible promoter. Examples of inducible promoters include, but are not limited to a metallothionine promoter, a glucocorticoid promoter, a progesterone promoter, and a tetracycline promoter.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another.

In order to assess the expression of an antibody polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene. Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art.

See, for example, Sambrook et al. (2001, Molecular Cloning: A Laboratory Manual, Cold Spring Harbor Laboratory, New York).

Biological methods for introducing a polynucleotide of interest into a host cell include the use of DNA and RNA vectors. Viral vectors, and especially retroviral vectors, have become the most widely used method for inserting genes into mammalian, e.g., human cells.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes. Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc, (Birmingham, Ala.).

Pharmaceutical Composition

Also disclosed is a pharmaceutical composition comprising a disclosed molecule in a pharmaceutically acceptable carrier. Pharmaceutical carriers are known to those skilled in the art. These most typically would be standard carriers for administration of drugs to humans, including solutions such as sterile water, saline, and buffered solutions at physiological pH. For example, suitable carriers and their formulations are described in Remington: The Science and Practice of Pharmacy (21 ed.) ed. PP. Gerbino, Lippincott Williams & Wilkins, Philadelphia, Pa. 2005. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. The solution should be RNAse free. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Methods of Treatment

Also disclosed is a method for treating a CD123-expressing cancer in a subject by administering to the subject a therapeutically effective amount of the disclosed pharmaceutical composition.

The disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

The compositions disclosed herein may be administered prophylactically to patients or subjects who are at risk for a CD123-expressing cancer. Thus, the method can further comprise identifying a subject at risk for a CD123-expressing cancer prior to administration of the herein disclosed compositions.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. A typical daily dosage of the disclosed composition used alone might range from about 1 µg/kg to up to 100 mg/kg of body weight or more per day, depending on the factors mentioned above.

In some embodiments, the molecule is administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of molecule containing lenalidomide administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

The cancer of the disclosed methods can be any CD123-expressing cell in a subject undergoing unregulated growth, invasion, or metastasis. Cancers that express CD123 include prostate cancer, ovarian cancer, adenocarcinoma of the lung, breast cancer, endometrial cancer, gastric cancer, colon cancer, and pancreatic cancer. CD123 has also been found on Jurkat cells. In some aspects, the cancer is a gallbladder cancer, exocrine adenocarcinoma, or apocrine adenocarcinomas.

In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, endometrial cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

The disclosed antibodies can be used in combination with any compound, moiety or group which has a cytotoxic or cytostatic effect. Drug moieties include chemotherapeutic agents, which may function as microtubulin inhibitors, mitosis inhibitors, topoisomerase inhibitors, or DNA intercalators, and particularly those which are used for cancer therapy.

The disclosed antibodies can be used in combination with a checkpoint inhibitor. The two known inhibitory checkpoint pathways involve signaling through the cytotoxic T-lymphocyte antigen-4 (CTLA-4) and programmed-death 1 (PD-1) receptors. These proteins are members of the CD28-B7 family of cosignaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. Checkpoint inhibitors include, but are not limited to antibodies that block PD-1 (Nivolumab (BMS-936558 or MDX1106), CT-011, MK-3475), PD-L1 (MDX-1105 (BMS-936559), MPDL3280A, MSB0010718C), PD-L2 (rHIgM12B7), CTLA-4 (Ipilimumab (MDX-010), Tremelimumab (CP-675,206)), IDO, B7-H3 (MGA271), B7-H4, TIM3, LAG-3 (BMS-986016).

Human monoclonal antibodies to programmed death 1 (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

In some embodiments, the PDL1 inhibitor comprises an antibody that specifically binds PDL1, such as BMS-936559 (Bristol-Myers Squibb) or MPDL3280A (Roche). In some embodiments, the PD1 inhibitor comprises an antibody that specifically binds PD1, such as lambrolizumab (Merck), nivolumab (Bristol-Myers Squibb), or MEDI4736 (AstraZeneca). Human monoclonal antibodies to PD-1 and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

The disclosed antibodies can be used in combination with other cancer immunotherapies. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rituxan, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

Generating optimal "killer" CD8 T cell responses also requires T cell receptor activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors.

In some embodiments, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In some embodiments, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In some embodiments, such an additional therapeutic agent may be selected from an anti-mitotic agent, such as taxanes, for instance docetaxel, and paclitaxel, and vinca alkaloids, for instance vindesine, vincristine, vinblastine, and vinorelbine.

In some embodiments, such an additional therapeutic agent may be selected from a topoisomerase inhibitor, such as topotecan or irinotecan, or a cytostatic drug, such as etoposide and teniposide.

In some embodiments, such an additional therapeutic agent may be selected from a growth factor inhibitor, such as an inhibitor of ErbBI (EGFR) (such as an EGFR antibody, e.g. zalutumumab, cetuximab, panitumumab or nimotuzumab or other EGFR inhibitors, such as gefitinib or erlotinib), another inhibitor of ErbB2 (HER2/neu) (such as a HER2 antibody, e.g. trastuzumab, trastuzumab-DM I or pertuzumab) or an inhibitor of both EGFR and HER2, such as lapatinib).

In some embodiments, such an additional therapeutic agent may be selected from a tyrosine kinase inhibitor, such as imatinib (Glivec, Gleevec ST1571) or lapatinib.

Therefore, in some embodiments, a disclosed antibody is used in combination with ofatumumab, zanolimumab, daratumumab, ranibizumab, nimotuzumab, panitumumab, hu806, daclizumab (Zenapax), basiliximab (Simulect), infliximab (Remicade), adalimumab (Humira), natalizumab (Tysabri), omalizumab (Xolair), efalizumab (Raptiva), and/or rituximab.

In some embodiments, a therapeutic agent for use in combination with antibodies as described above may be an anti-cancer cytokine, chemokine, or combination thereof. Examples of suitable cytokines and growth factors include IFNy, IL-2, IL-4, IL-6, IL-7, IL-10, IL-12, IL-13, IL-15, IL-18, IL-23, IL-24, IL-27, IL-28a, IL-28b, IL-29, KGF, IFNa (e.g., INFa2b), IFN , GM-CSF, CD40L, Flt3 ligand, stem cell factor, ancestim, and TNFa. Suitable chemokines may include Glu-Leu-Arg (ELR)-negative chemokines such as IP-10, MCP-3, MIG, and SDF-Ia from the human CXC and C-C chemokine families. Suitable cytokines include cytokine derivatives, cytokine variants, cytokine fragments, and cytokine fusion proteins.

In some embodiments, a therapeutic agent for use in combination with antibodies as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos. 6,440,735 and 6,713,055) . Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and anti-sense Bcl-2.

In some embodiments, a therapeutic agent for use in combination with antibodies as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxy-progesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

In some embodiments, a therapeutic agent for use in combination with antibodies as described above may be an anti-cancer nucleic acid or an anti-cancer inhibitory RNA molecule.

Combined administration, as described above, may be simultaneous, separate, or sequential. For simultaneous administration the agents may be administered as one composition or as separate compositions, as appropriate.

In some embodiments, the disclosed antibodies are administered in combination with radiotherapy. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In some embodiments, the disclosed antibodies are administered in combination with surgery.

DEFINITIONS

The term "amino acid sequence" refers to a list of abbreviations, letters, characters or words representing amino acid residues. The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class from any species, including any of the human classes: IgG, IgM, IgA, IgD, and IgE. In exemplary embodiments, antibodies used with the methods and compositions described herein are derivatives of the IgG class. In addition to intact immunoglobulin molecules, also included in the term "antibodies" are fragments or polymers of those immunoglobulin molecules, and human or humanized versions of immunoglobulin molecules that selectively bind the target antigen.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')2, scFv, Fv, dsFv diabody, Fc, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The term "antigen binding site" refers to a region of an antibody that specifically binds an epitope on an antigen.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "chimeric molecule" refers to a single molecule created by joining two or more molecules that exist separately in their native state. The single, chimeric molecule has the desired functionality of all of its constituent molecules. One type of chimeric molecules is a fusion protein.

The term "engineered antibody" refers to a recombinant molecule that comprises at least an antibody fragment comprising an antigen binding site derived from the variable domain of the heavy chain and/or light chain of an antibody and may optionally comprise the entire or part of the variable and/or constant domains of an antibody from any of the Ig classes (for example IgA, IgD, IgE, IgG, IgM and IgY).

The term "epitope" refers to the region of an antigen to which an antibody binds preferentially and specifically. A monoclonal antibody binds preferentially to a single specific epitope of a molecule that can be molecularly defined. In the present invention, multiple epitopes can be recognized by a multispecific antibody.

The term "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The term "Fab fragment" refers to a fragment of an antibody comprising an antigen-binding site generated by cleavage of the antibody with the enzyme papain, which cuts at the hinge region N-terminally to the inter-H-chain disulfide bond and generates two Fab fragments from one antibody molecule.

The term "F(ab')2 fragment" refers to a fragment of an antibody containing two antigen-binding sites, generated by cleavage of the antibody molecule with the enzyme pepsin which cuts at the hinge region C-terminally to the inter-H-chain disulfide bond.

The term "Fc fragment" refers to the fragment of an antibody comprising the constant domain of its heavy chain.

The term "Fv fragment" refers to the fragment of an antibody comprising the variable domains of its heavy chain and light chain. "Gene construct" refers to a nucleic acid, such as a vector, plasmid, viral genome or the like which includes a "coding sequence" for a polypeptide or which is otherwise transcribable to a biologically active RNA (e.g., antisense, decoy, ribozyme, etc), may be transfected into cells, e.g. in certain embodiments mammalian cells, and may cause expression of the coding sequence in cells transfected with the construct. The gene construct may include one or more regulatory elements operably linked to the coding sequence, as well as intronic sequences, polyadenylation sites, origins of replication, marker genes, etc.

The term "identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

The term "linker" is art-recognized and refers to a molecule or group of molecules connecting two compounds, such as two polypeptides. The linker may be comprised of a single linking molecule or may comprise a linking molecule and a spacer molecule, intended to separate the linking molecule and a compound by a specific distance.

The term "multivalent antibody" refers to an antibody or engineered antibody comprising more than one antigen recognition site. For example, a "bivalent" antibody has two antigen recognition sites, whereas a "tetravalent" antibody has four antigen recognition sites. The terms "monospecific", "bispecific", "trispecific", "tetraspecific", etc. refer to the number of different antigen recognition site specificities (as opposed to the number of antigen recognition sites) present in a multivalent antibody. For example, a "monospecific" antibody's antigen recognition sites all bind the same epitope. A "bispecific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The terms "peptide," "protein," and "polypeptide" are used interchangeably to refer to a natural or synthetic molecule comprising two or more amino acids linked by the carboxyl group of one amino acid to the alpha amino group of another.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The terms "polypeptide fragment" or "fragment", when used in reference to a particular polypeptide, refers to a polypeptide in which amino acid residues are deleted as compared to the reference polypeptide itself, but where the remaining amino acid sequence is usually identical to that of the reference polypeptide. Such deletions may occur at the amino-terminus or carboxy-terminus of the reference polypeptide, or alternatively both. Fragments typically are at least about 5, 6, 8 or 10 amino acids long, at least about 14 amino acids long, at least about 20, 30, 40 or 50 amino acids long, at least about 75 amino acids long, or at least about 100, 150, 200, 300, 500 or more amino acids long. A fragment can retain one or more of the biological activities of the reference polypeptide. In various embodiments, a fragment may comprise an enzymatic activity and/or an interaction site of the reference polypeptide. In another embodiment, a fragment may have immunogenic properties.

The term "protein domain" refers to a portion of a protein, portions of a protein, or an entire protein showing structural integrity; this determination may be based on amino acid composition of a portion of a protein, portions of a protein, or the entire protein.

The term "single chain variable fragment or scFv" refers to an Fv fragment in which the heavy chain domain and the light chain domain are linked. One or more scFv fragments may be linked to other antibody fragments (such as the constant domain of a heavy chain or a light chain) to form antibody constructs having one or more antigen recognition sites.

A "spacer" as used herein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The terms "transformation" and "transfection" mean the introduction of a nucleic acid, e.g., an expression vector, into a recipient cell including introduction of a nucleic acid to the chromosomal DNA of said cell.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 70%, 80%, 90%, 95%, 96%, 97%, 98%, 99% sequence identity to a reference sequence.

The term "vector" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element).

A number of embodiments of the invention have been described. Nevertheless, it will be understood that various modifications may be made without departing from the spirit and scope of the invention. Accordingly, other embodiments are within the scope of the following claims.

EXAMPLES

Example 1: Screen for Anti-AML Antibodies

EL4 mouse lymphoma cells that express immunogen or irrelevant antigen were screened for anti-AML antibody binding. As shown in FIG. 1, EL4-empty, EL4-CD123, and EL4-CD33 cells were incubated together in each well of a 96 well plate. In addition an anti-CD123 PE antibody and hybridoma antibody, with putative anti-C33 reactivity, was included in the culture. The antibodies and cells were co-incubated, washed, and stained with Rat anti-mouse IgG APC. Positive binding was revealed by flow cytometry as anti-CD33/APC$^+$ and anti-CD123/PE$^-$.

Figure 2:
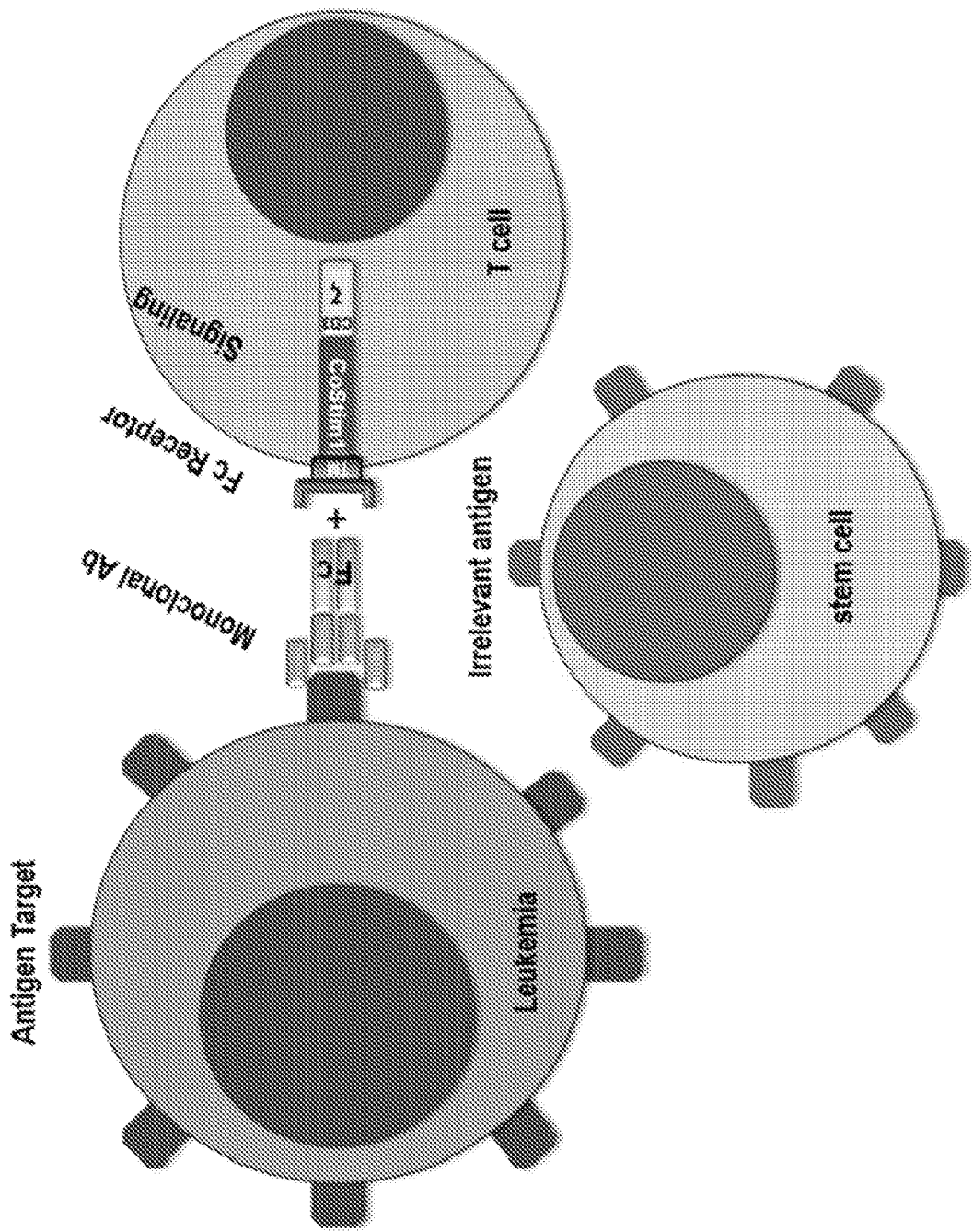
FIG. 2 illustrates secondary screening method for functional antibodies.

As illustrated in FIG. 2, chosen antibodies were subjected to a secondary, functional screening with Jurkat cells that express a CAR docking platform for antibodies and target cells. These antibodies were screened for T cell activation. 150 clones were selected based on EL4 binding. EL4 CD123 (target) and CD33 (negative control) were incubated with Jurkat mCD16 or mCD32 with its NFKB/RE GFP reporter. See Tables 1 and 2.

TABLE 1

| | | | | | | | | | | | | |
|---|---|---|---|---|---|---|---|---|---|---|---|---|
| CD33 | 1A9 | 1B1 | 2H1 | 2H11 | 3D2 | 3E5 | 3F5 | 4E4 | 4E10 | 4F2 | 4G11 | 6A5 |
| | 7C1 | 7C12 | 7F7 | 9B12 | 9C5 | 9E10 | 9F12 | 9H6 | 10A12 | 10C11 | 10D8 | 11F12 |
| | 12B4 | 12F7 | 12F8 | 12G3 | 12G11 | 12H3 | 12H5 | 12H11 | 15A9 | 15A12 | 15E1 | 15G5 |
| | 16B5 | 17D2 | 17E7 | 17E9 | 21B12 | 22E7 | 24C5 | 32G4 | NS | L/D | CD123 | NO SUP |
| CD123 | 1A9 | 1B1 | 2H1 | 2H11 | 3D2 | 3E5 | 3F5 | 4E4 | 4E10 | 4F2 | 4G11 | 6A5 |
| | 7C1 | 7C12 | 7F7 | 9B12 | 9C5 | 9E10 | 9F12 | 9H6 | 10A12 | 10C11 | 10D8 | 11F12 |
| | 12B4 | 12F7 | 12F8 | 12G3 | 12G11 | 12H3 | 12H5 | 12H11 | 15A9 | 15A12 | 15E1 | 15G5 |
| | 16B5 | 17D2 | 17E7 | 17E9 | 21B12 | 22E7 | 24C5 | 32G4 | NS | L/D | CD123 | NO SUP |

CD33 = $1.53 \times 10^6$/ml = $30.6 \times 10^6$ total, 75% Live

CD123 = $4.28 \times 10^5$/ml = $20.1 \times 10^6$ total, 83% Live

TABLE 2

| Clone | CD123/APC+ | CD33/APC+ | Difference |
|---|---|---|---|
| 3F5 | 98.9 | 51.99 | 46.91 |
| 4E4 | 90.36 | 38.52 | 51.84 |
| 4E10 | 98.11 | 55.59 | 42.52 |
| 10C11 | 99 | 42.34 | 56.66 |
| 12H3 | 57.94 | 21 | 36.94 |
| 12H5 | 81.94 | 13.4 | 68.54 |
| 12H11 | 99.14 | 14.29 | 84.85 |
| 15A9 | 99.14 | 40.28 | 58.86 |
| 15A12 | 99.32 | 57.06 | 42.26 |
| 15G5 | 10.34 | 11.02 | −0.68 |
| 16135 | 10.39 | 2.32 | 8.07 |
| 17E7 | 95.93 | 10.41 | 85.52 |

Figure 3:
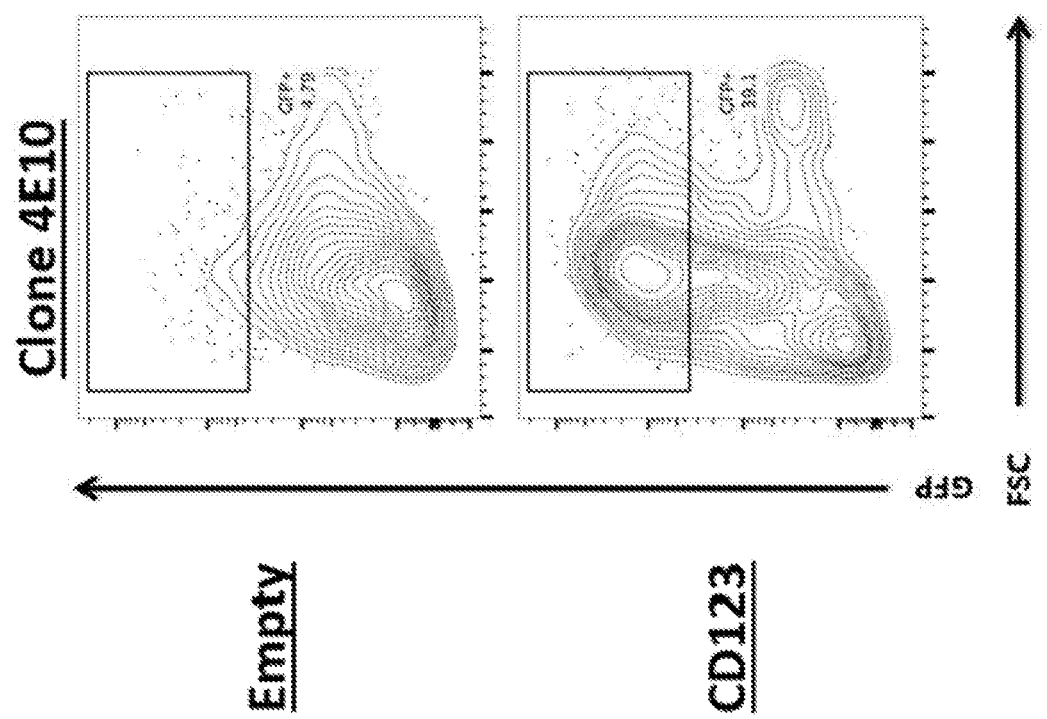
FIG. 3 shows Jurkat T cell activation measured by GFP flow cytometry for cultured EL4-CD123 or EL4-CD33 targets, hybridoma antibodies, and Jurkat cells modified to include either a CD16 or CD32 Fc receptor conjugated to human 41BB and CD3zeta.
Figure 4A:
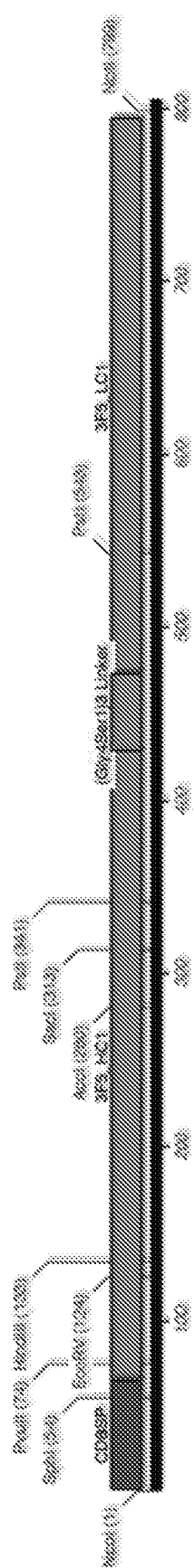
FIGS. 4A to 4H are CD123 CAR diagrams for 3F5HC1_LC (FIG. 4A), 12H1HC1_LC1 (FIG. 4B), 12H1HC2_LC1 (FIG. 4C), 12H2HC1_LC1 (FIG. 4D), 15A12HC1_LC1 (FIG. 4E), 15A12HC1_LC2 (FIG. 4F), 15A12HC2_LC1 (FIG. 4G), and 15A12HC2_LC2 (FIG. 4H).
Figure 4B:
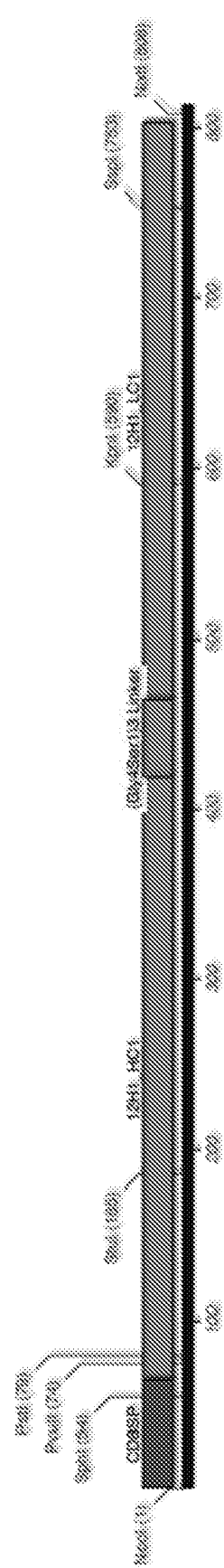
Figure 4C:
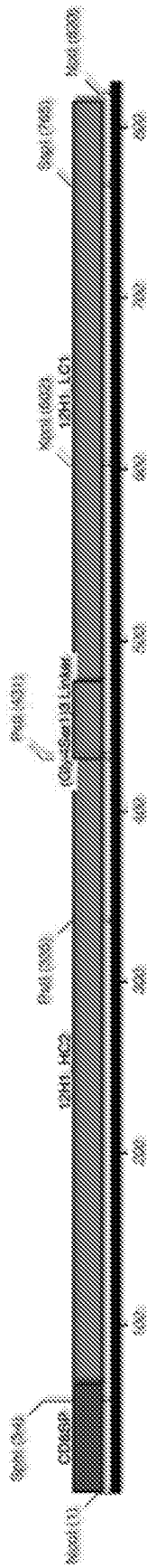
Figure 4D:
Figure 4E:
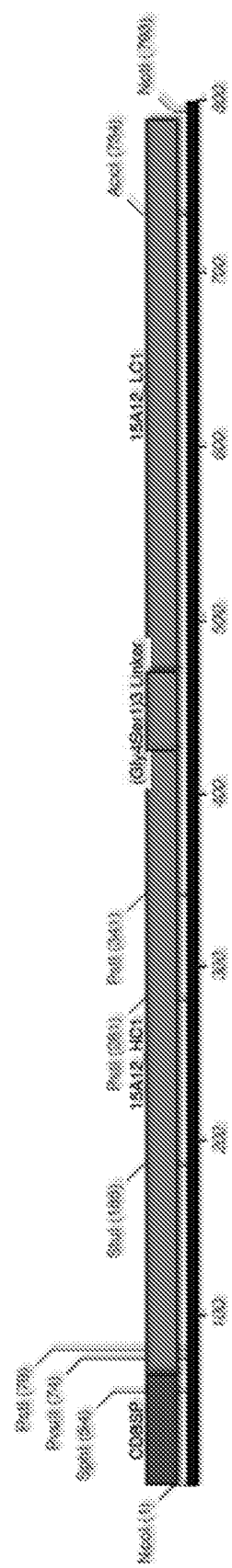
Figure 4F:
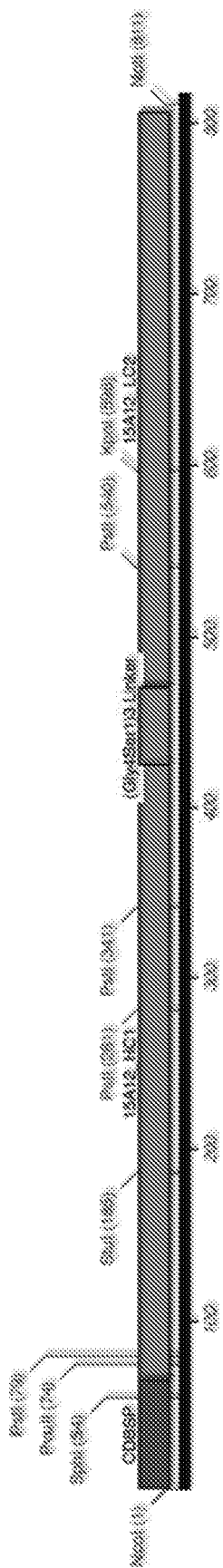
Figure 4G:
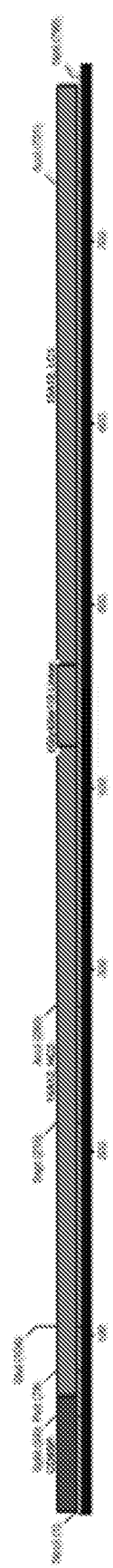
Figure 4H:
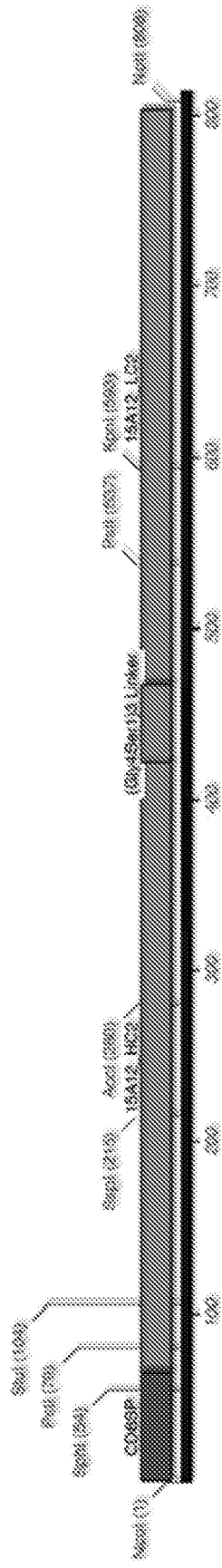

12 clones were selected for EL4-CD123 validation using CHO CD123 (target) or empty (negative control) and Jurkat mCD16-GFP or mCD32 as a reporter. $1\times10^4$ CHO cells were cultured into wells of a 96 well plate. Hybridoma supernatant (3G5, 4E4, etc), which included the putative anti-AML antibodies, were added to the culture media. Jurkat cells were modified to include either a CD16 or CD32 Fc receptor conjugated to human 41BB and CD3zeta. In addition, these Jurkat cells have a transgene GFP that is controlled by NFKB-responsive elements. The EL4 targets, hybridoma antibodies, and $1\times10^4$ Jurkat cells were incubated overnight and antibody ligation and Jurkat T cell activation was measured by GFP flow cytometry (FIG. 3).

CD123 Clones were selected after EL4 binding and Jurkat activation screening (Table 3).

TABLE 3

| Hybridoma Clone | Binding (APC+ %) | Activation (GFP+ %) |
|---|---|---|
| 27A3 | 55 | 37 |
| 33G3 | 63 | 35 |
| 36C2 | 70 | 34 |
| 6A11 | 2 | 20 |
| 35D5 | 63 | 7 |
| 38G5 | 56 | 6 |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A recombinant antibody that selectively binds CD123 on tumor cells, comprising a variable heavy ($V_H$) domain having CDR1, CDR2 and CDR3 sequences and a variable light ($V_L$) domain having CDR1, CDR2 and CDR3 sequences, wherein the CDR1 sequence of the $V_H$ domain comprises the amino acid sequence GYTFTDYN (SEQ ID NO:1), the CDR2 sequence of the $V_H$ domain comprises the amino acid sequence INPNNGGT (SEQ ID NO:2), the CDR3 sequence of the $V_H$ domain comprises the amino acid sequence ARKGYGGNYDYFDY (SEQ ID NO:3), ALYYYGGSLDY (SEQ ID NO:11), the CDR1 sequence of the $V_L$ comprises the amino acid sequence QSIGTS (SEQ ID NO:4), the CDR2 sequence of the $V_L$ domain comprises the amino acid sequence YASX (SEQ ID NO:5), and the CDR3 sequence of the $V_L$ domain comprises the amino acid sequence QQSNSWPYT (SEQ ID NO:6) or QQYYSYPRT (SEQ ID NO:15);

the CDR1 sequence of the $V_H$ domain comprises the amino acid sequence GFNIKDTY (SEQ ID NO:7) or GFSLSTYGMG (SEQ ID NO:8), the CDR2 sequence of the $V_H$ domain comprises the amino acid sequence IDPANGNT (SEQ ID NO:9) or IYWDDDK (SEQ ID NO:10), the CDR3 sequence of the $V_H$ domain comprises the amino acid sequence ALYYYGGSLDY (SEQ ID NO:11) or AQSLIYDGYYGFAY (SEQ ID NO:12), the CDR1 sequence of the $V_L$ comprises the amino acid sequence QSLLYSGNQKNY (SEQ ID NO:13), the CDR2 sequence of the $V_L$ domain comprises the amino acid sequence WASX (SEQ ID NO:14), and the CDR3 sequence of the $V_L$ domain comprises the amino acid sequence QQYYSYPRT (SEQ ID NO:15);

the CDR1 sequence of the $V_H$ domain comprises the amino acid sequence GYTFTYYG (SEQ ID NO:16), the CDR2 sequence of the $V_H$ domain comprises the amino acid sequence INTYSGVP (SEQ ID NO:17), the CDR3 sequence of the $V_H$ domain comprises the amino acid sequence ARWIYYSDLYGMDY (SEQ ID NO:18), the CDR1 sequence of the $V_L$ comprises the amino acid sequence QSIVHSNGDTY (SEQ ID NO:19), the CDR2 sequence of the $V_L$ domain comprises the amino acid sequence KVSX (SEQ ID NO:20), and the CDR3 sequence of the $V_L$ domain comprises the amino acid sequence FQGSHVPWT (SEQ ID NO:21); or the CDR1 sequence of the $V_H$ domain comprises the amino acid sequence GYTFSSYW (SEQ ID NO:22) or GYTLTTYL (SEQ ID NO:23), the CDR2 sequence of the $V_H$ domain comprises the amino acid sequence INPSSGYT (SEQ ID NO:24) or INPNSGSS (SEQ ID NO:25), the CDR3 sequence of the $V_H$ domain comprises the amino acid sequence ARDGNYDHWYFDV (SEQ ID NO:26) or AIRHYGGSLFDY (SEQ ID NO:27), the CDR1 sequence of the $V_L$ comprises the amino acid sequence QDINSY (SEQ ID NO:28) or QSLLNSRTRKNY (SEQ ID NO:29), the CDR2 sequence of the $V_L$ domain comprises the amino acid sequence RANX (SEQ ID NO:30), and the CDR3 sequence of the $V_L$ domain comprises the amino acid sequence LQYDELLT (SEQ ID NO:31) or EQSYNLFT (SEQ ID NO:32).

2. The recombinant antibody of claim 1, wherein the $V_H$ domain comprises the amino acid sequence SEQ ID NO:33, SEQ ID NO:34, SEQ ID NO:35, SEQ ID NO:36, SEQ ID NO:37, or SEQ ID NO:38.

3. The recombinant antibody of claim 1, wherein the $V_L$ domain comprises the amino acid sequence SEQ ID NO:39, SEQ ID NO:40, SEQ ID NO:41, SEQ ID NO:42, or SEQ ID NO:43.

4. The recombinant antibody of claim 1, wherein the antibody is a single chain antibody (scFv) comprising the amino acid sequence SEQ ID NO:44, SEQ ID NO:45, SEQ ID NO:46, SEQ ID NO:47, SEQ ID NO:48, SEQ ID NO:49, SEQ ID NO:50, or SEQ ID NO:51.

5. An isolated nucleic acid sequence encoding the recombinant antibody of claim 1.

6. A vector comprising the isolated nucleic acid sequence of claim 5.

7. A cell comprising the vector of claim 6.

8. A method for treating cancer in a subject, comprising administering to the subject a therapeutically effective amount of the recombinant antibody of claim 1 in a pharmaceutically acceptable carrier.

9. The method of claim 8, further comprising administering to the subject a checkpoint inhibitor.

10. The method of claim 9, wherein the checkpoint inhibitor comprises an anti-PD-1 antibody, anti-PD-L1 antibody, anti-CTLA-4 antibody, or a combination thereof.

11. The method of claim 8, wherein the cancer comprises Acute Myeloid Leukemia (AML), blastic plasmocytoid dendritic cell neoplasm, hairy cell leukemia, or Acute Lymphoblastic Leukemia.

* * * * *